(12) United States Patent
Musil et al.

(10) Patent No.: US 6,323,155 B1
(45) Date of Patent: Nov. 27, 2001

(54) 4-BENZOYL ISOXAZOLES DERIVATIVES AND THEIR USE AS HERBICIDES

(75) Inventors: Tibor Musil; Simon Neil Pettit; Philip Henry Gaunt Smith, all of Ongar (GB)

(73) Assignee: Rhone-Poulenc Agriculture Limited, Ongar (GB)

( * ) Notice: Subject to any disclaimer, the term of this patent is extended or adjusted under 35 U.S.C. 154(b) by 0 days.

(21) Appl. No.: 08/454,370

(22) PCT Filed: Dec. 15, 1993

(86) PCT No.: PCT/EP93/03537

§ 371 Date: Nov. 1, 1995

§ 102(e) Date: Nov. 1, 1995

(87) PCT Pub. No.: WO94/14782

PCT Pub. Date: Jul. 7, 1994

(30) Foreign Application Priority Data

Dec. 18, 1992 (GB) ............................................ 9226396
May 18, 1993 (GB) ............................................ 9310204

(51) Int. Cl.[7] ........................... A01N 43/80; C07D 261/06
(52) U.S. Cl. .................................... 504/271; 548/248
(58) Field of Search ............................. 548/248; 504/271

(56) References Cited

U.S. PATENT DOCUMENTS

| | | | |
|---|---|---|---|
| 5,366,957 | * 11/1994 | Cain et al. | 548/248 |
| 5,371,064 | * 12/1994 | Cramp et al. | 548/248 |
| 5,489,570 | * 2/1996 | Geach et al. | 548/248 |

FOREIGN PATENT DOCUMENTS

| | | |
|---|---|---|
| 0418175 | 3/1991 | (EP) . |
| 0487357 | 5/1992 | (EP) . |

OTHER PUBLICATIONS

Cram and Hammond, "Organic Chemistry", McGraw–Hill Book Co. N.Y. (1964) 2nd Ed. pp 565–567.*

* cited by examiner

Primary Examiner—Patricia L. Morris
(74) Attorney, Agent, or Firm—Burns, Doane, Swecker & Mathis, L.L.P.

(57) ABSTRACT

4-Benzoylisoxazole derivatives of the formula

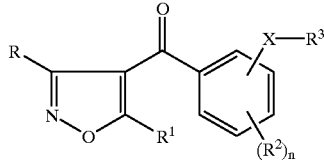

(I)

wherein R is H or an ester; $R^1$ is alkyl, haloalkyl or optionally substituted cycloalkyl; $R^2$ is halogen, optionally halogenated alkyl, alkenyl or alkynyl; alkyl substituted with one or more —$OR^5$; —$NO_2$, —CN, —$CO_2R^5$, —$S(O)_pR^6$, —$O(CH_2)_mOR^5$, —$COR^5$, —$NR^5R^6$, —$N(R^8)SO_qR^7$, —$CONR^9R^{10}$ or —$OR^{51}$; or optionally substituted phenyl; $R^3$ is —$S(O)_qR^7$; X is —$N(R^8)$—; n is 0, 1, 2, 3, or 4; $R^5$, $R^{51}$ and $R^6$ are independently H; optionally halogenated alkyl, alkenyl or alkynyl; optionally substituted phenyl; or cycloalkyl; $R^7$ is optionally halogenated alkyl, alkenyl or alkynyl; cycloalkyl; optionally substituted phenyl; or optionally substituted amino; $R^8$ is H; optionally halogenated alkyl, alkenyl or alkynyl; cycloalkyl; optionally substituted phenyl; or alkoxy; m is 1, 2 or 3; p is 0, 1 or 2; q is 0 or 2; and their use as herbicides are described.

44 Claims, No Drawings

4-BENZOYL ISOXAZOLES DERIVATIVES AND THEIR USE AS HERBICIDES

This invention relates to novel 4-benzoylisoxazole derivatives, compositions containing them, processes for their preparation, intermediates in their preparation and their use as herbicides.

Herbicidal 4-benzoylisoxazoles are described in European Patent Publication Number 0418175.

The present invention provides 4-benzoylisoxazole derivatives of formula (I):

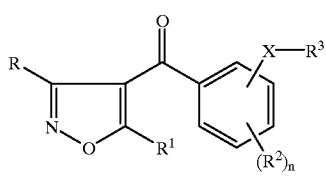

wherein:
R represents the hydrogen atom or a group —$CO_2R^4$;
$R^1$ represents:
a straight- or branched-chain alkyl group containing up to six carbon atoms which is optionally substituted by one or more halogen atoms; or
a cycloalky group containing from three to six carbon atoms optionally substituted by one or more $R^5$ groups or one or more halogen atoms;
$R^2$ represents:
a halogen atom;
a straight- or branched-chain allyl, alkenyl or alkynyl group containing up to six carbon atoms optionally substituted by one or more halogen atoms;
a straight- or branched-chain alkyl group containing up to six carbon atoms which is substituted by one or more groups —$OR^5$;
a group selected from nitro, cyano, —$CO_2R^5$, —$S(O)_pR^6$, —$O(CH_2)_mOR^5$, —$COR^5$, —$NR^5R^6$, —$N(R^8)SO_qR^7$, —$CONR^9R^{10}$ and —$OR^{51}$;
phenyl optionally substituted by from one to three groups $R^{21}$ which may be the same or different;
$R^3$ represents —$S(O)_qR^7$;
X represents a group —$N(R^8)$—;
n represents zero or an integer from one to four; where n is greater than one the groups $R^2$ may be the same or different;
$R^4$ represents a straight- or branched-chain alkyl group containing up to six carbon atoms optionally substituted by one or more halogen atoms;
$R^5$, $R^{51}$ and $R^6$, which may be the same or different, each represents:
the hydrogen atom;
a straight- or branched-chain alkyl, alkenyl or alkynyl group containing up to six carbon atoms optionally substituted by one or more halogen atoms;
phenyl optionally substituted by from one to five groups $R^2$ which may be the same or different; or
a cycloalkyl group containing from three to six carbon atoms;
$R^7$ represents:
a straight- or branched-chain alkyl, alkenyl or alkynyl group containing up to six carbon atoms optionally substituted by one or more halogen atoms;

a cycloalkyl group containing from three to six carbon atoms;
phenyl or benzyl optionally substituted by from one to five groups $R^{21}$ which may be the same or different;
or —$NR^9R^{10}$;
$R^8$ represents:
the hydrogen atom;
a straight- or branched-chain alkyl, alkenyl or alkynyl group containing up to ten carbon atoms optionally substituted by one or more halogen atoms;
a cycloalkyl group containing from three to six carbon atoms;
phenyl optionally substituted by from one to five groups which may be the same or different selected from halogen, nitro, cyano, $R^5$, $S(O)_pR^5$ and —$OR^5$; or
a group —$OR^{11}$;
$R^9$ represents:
the hydrogen atom;
a straight- or branched-chain alkyl group containing up to six carbon atoms optionally substituted by one or more halogen atoms;
or phenyl optionally substituted by from one to five groups $R^2$ which may be the same or different;
$R^{10}$ represents a group selected from $R^5$ and —$OR^{11}$;
or $R^9$ and $R^{10}$, together with the nitrogen to which they are attached, may form a 5 or 6 membered ring optionally containing an oxygen or nitrogen atom in the ring (e.g. pyrrolidine, morpholine, pyrrole, piperidine and piperazine), wherein the ring is optionally substituted by one or more alkyl groups containing up to 3 carbon atoms;
$R^{11}$ represents a straight- or branched-chain alkyl group containing up to six carbon atoms;
$R^{21}$ represents:
a halogen atom;
a straight- or branched-chain alkyl group containing up to three carbon atoms optionally substituted by one or more halogen atoms;
or a group selected from nitro, cyano, —$S(O)_pR^5$ and —$OR^5$;
m represents one, two or three; and
p represents zero, one or two;
q represents zero or two;
and agriculturally acceptable salts thereof, which possess valuable herbicidal properties.

Furthermore in certain cases the groups R, $R^1$, $R^2$, and $R^3$ may give rise to geometric and/or optical isomers. All such forms are embraced by the present invention.

By the term "agriculturally acceptable salts" is meant salts the cations or anions of which are known and accepted in the art for the formation of salts for agricultural or horticultural use. Preferably the salts are water-soluble.

The compounds of the invention, in some aspects of their activity, for example in their control of important weeds found in cereal crops, e.g. *Galium aparine* and *Avena fatua*, and in their selectivity in important cereal crops, e.g. wheat, show advantages over known compounds.

It will be understood that in the above definition $R^2$ does not include substituents containing two or more phenyl rings linked through a bridging group.

In one embodiment the invention provides compounds of formula I above wherein:

R represents the hydrogen atom or a group —$CO_2R^4$;

$R^1$ represents:

a straight- or branched-chain alkyl group containing up to six carbon atoms which is optionally substituted by one or more halogen atoms; or a cycloalkyl group containing from three to six carbon atoms optionally substituted by one or more $R^5$ groups;

$R^2$ represents:

a straight- or branched-chain alkyl, alkenyl or alkynyl group containing up to six carbon atoms optionally substituted by one or more halogen atoms;

a straight- or branched-chain alkyl group containing up to six carbon atoms which is substituted by a group —$OR^5$;

a halogen atom;

phenyl optionally substituted by from one to three groups $R^{21}$ which may be the same or different;

a group selected from —$COR^5$, nitro, cyano, —$CO_2R^5$, —$S(O)_pR^6$, —$O(CH_2)_mOR^5$, —$N(R^8)SO_2R^7$, —$CONR^9R^{10}$ and —$OR^{51}$;

$R^3$ represents —$S(O)_qR^7$;

X represents a group —$N(R^8)$—;

n represents zero or an integer from one to four; where n is greater than one the groups $R^2$ may be the same or different;

$R^4$ represents a straight- or branched-chain alkyl group containing up to six carbon atoms optionally substituted by one or more halogen atoms;

$R^5$ represents:

a straight- or branched-chain alkyl, alkenyl or alkynyl group containing up to six carbon atoms optionally substituted by one or more halogen atoms; or a cycloalkyl group containing from three to six carbon atoms;

$R^{51}$ represents:

a straight- or branched-chain alkyl, alkenyl or alkynyl group containing up to six carbon atoms optionally substituted by one or more halogen atoms;

a cycloalkyl group containing from three to six carbon atoms;

or phenyl optionally substituted by from one to five groups which may be the same or different selected from a halogen atom, a straight- or branched-chain alkyl group containing up to three carbon atoms optionally substituted by one or more halogen atoms; nitro, cyano, —$S(O)_pR^5$ and —$OR^5$;

$R^6$ represents:

a straight- or branched-chain akyl, alkenyl or alkynyl group containing up to six carbon atoms optionally substituted by one or more halogen atoms;

a cycloalkyl group containing from three to six carbon atoms;

or phenyl optionally substituted by from one to five groups which may be the same or different selected from a halogen atom, a straight- or branched-chain alkyl group containing up to three carbon atoms optionally substituted by one or more halogen atoms; nitro, cyano, —$S(O)_pR^5$ and —$OR^5$;

$R^7$ represents:

a straight- or branched-chain alkyl, alkenyl or alkynyl group containing up to six carbon atoms optionally substituted by one or more halogen atoms;

a cycloalkyl group containing from three to six carbon atoms;

phenyl optionally substituted by from one to five groups $R^{21}$ which may be the same or different;

or —$NR^9R^{10}$;

$R^8$ represents:

the hydrogen atom; or a straight- or branched-chain alkyl, alkenyl or alkynyl group containing up to six carbon atoms optionally substituted by one or more halogen atoms;

a cycloalkyl group containing from three to six carbon atoms;

phenyl optionally substituted by from one to five groups which may be the same or different selected from a halogen atom, a straight- or branched-chain alkyl group containing up to three carbon atoms optionally substituted by one or more halogen atoms; nitro, cyano, —$S(O)_pR^5$ and —$OR^5$;

or a group —$OR^{11}$;

$R^9$ represents hydrogen or a straight- or branched-chain alkyl group containing up to six carbon atoms optionally substituted by one or more halogen atoms;

$R^{10}$ represents a group selected from $R^5$ and —$OR^{11}$;

or $R^9$ and $R^{10}$, together with the nitrogen to which they are attached, may form a 5 or 6 membered ring optionally containing an oxygen or nitrogen atom in the ring (e.g. pyrrolidine, morpholine, pyrrole, piperidine and piperazine), wherein the ring is optionally substituted by one or more alkyl groups containing up to 3 carbon atoms;

$R^{11}$ represents a straight- or branched-chain alkyl group containing up to six carbon atoms;

$R^{21}$ represents:

a halogen atom;

a straight- or branched-chain alkyl group containing up to three carbon atoms optionally substituted by one or more halogen atoms; or a group selected from nitro, cyano, —$S(O)_pR^5$ and —$OR^5$;

m represents one, two or three; p represents zero, one or two;

and q represents two.

In a further embodiment the invention provides compounds of formula I above wherein:

R represents the hydrogen atom or a group —$CO_2R^4$;

$R^1$ represents:

a straight- or branched-chain alkyl group containing up to six carbon atoms which is optionally substituted by one or more halogen atoms; or a cycloalkyl group containing from three to six carbon atoms optionally substituted by one or more $R^5$ groups or one or more halogen atoms;

$R^2$ represents:

a halogen atom;

a straight- or branched-chain alkyl group containing up to six carbon atoms optionally substituted by one or more halogen atoms;

a straight- or branched-chain alkyl group containing up to six carbon atoms which is substituted by one or more groups —$OR^5$;

a group selected from nitro, cyano, —$CO_2R^5$, —$S(O)_pR^6$, —$O(CH_2)_mOR^5$, —$COR^5$, —$NR^5R^6$, —$N(R^8)SO_qR^7$ and —$OR^{51}$;

$R^3$ represents —$S(O)_qR^7$;

X represents a group —$N(R^8)$—;

n represents zero or an integer from one to four; where n is greater than one the groups $R^2$ may be the same or different;

$R^4$ represents a straight- or branched-chain alkyl group containing up to six carbon atoms which is optionally substituted by one or more halogen atoms;

$R^5$, $R^{51}$ and $R^6$, which may be the same or different, each represents:

the hydrogen atom;

a straight- or branched-chain alkyl group containing up to six carbon atoms which is optionally substituted by one or more halogen atoms;

phenyl optionally substituted by from one to five groups $R^2$ which may be the same or different;

$R^7$ represents:

a straight- or branched-chain alkyl group containing up to six carbon atoms which is optionally substituted by one or more halogen atoms;

phenyl optionally substituted by from one to five groups $R^{21}$ which may be the same or different; or a group —$NR^9R^{10}$;

$R^8$ represents:

the hydrogen atom;

a straight- or branched-chain alkyl, alkenyl or alkynyl group containing up to ten carbon atoms which is optionally substituted by one or more halogen atoms; or phenyl optionally substituted from one to five groups which may be the same or different selected from nitro, halogen, $R^5$ and —$OR^5$;

$R^9$ and $R^{10}$, which may be the same or different, each represents:

the hydrogen atom;

a straight- or branched-chain alkyl group containing up to six carbon atoms optionally substituted by one or more halogen atoms;

or phenyl optionally substituted by from one to five groups $R^2$ which may be the same or different;

$R^{21}$ represents:

a halogen atom;

a straight- or branched-chain alkyl group containing up to three carbon atoms optionally substituted by one or more halogen atoms;

or a group selected from nitro, cyano, —$S(O)_pR^6$ and —$OR^5$;

p represents zero, 1 or 2;

q represents zero or 2; and m represents 1, 2 or 3.

Preferably the 5- and 6-positions of the benzoyl ring are unsubstituted.

Preferably the 2-position of the benzoyl ring is substituted.

A preferred class of compounds of formula (I) are those wherein:

$R^1$ represents:

a straight- or branched-chain alkyl group containing up to six carbon atoms which is optionally substituted by one or more halogen atoms; or a cycloalkyl group containing from three to six carbon atoms optionally substituted by one or more methyl groups;

$R^2$ represents:

a halogen atom;

a straight- or branched-chain alkyl, alkenyl or alkynyl group containing up to six carbon atoms optionally substituted by one or more halogen atoms;

a straight- or branched-chain alkyl group containing up to six carbon atoms which is substituted by a group —$OR^5$;

phenyl optionally substituted by from one to three groups $R^{21}$ which may be the same or different;

or a group selected from —$COR^5$, cyano, nitro, —$CO_2R^5$, —$S(O)_pR^6$, —$O(CH_2)_mOR^5$, —$N(R^8)SO_2R^7$ and —$OR^{51}$;

n represents zero or an integer from one to three; where n is greater than one the groups $R^2$ may be the same or different;

$R^5$ represents:

a straight- or branched-chain alkyl group containing up to six carbon atoms optionally substituted by one or more halogen atoms;

or a cycloalkyl group containing from three to six carbon atoms;

$R^{51}$ and $R^6$, which may be the same or different, each represents:

a straight- or branched-chain alkyl or alkenyl group containing up to six carbon atoms optionally substituted by one or more halogen atoms;

a straight- or branched-chain alkynyl group containing from three to six carbon atoms;

a cycloalkyl group containing three to six carbon atoms;

$R^7$ represents:

a straight- or branched-chain alkyl or alkenyl group containing up to six carbon atoms optionally substituted by one or more halogen atoms;

a straight- or branched-chain alkynyl group containing from three to six carbon atoms;

a cycloalkyl group containing three to six carbon atoms; or phenyl optionally substituted by from one to three groups $R^{21}$ which may be the same or different;

$R^8$ represents:

the hydrogen atom; or a straight- or branched-chain alkyl or alkenyl group containing up to six carbon atoms optionally substituted by one or more halogen atoms;

a straight- or branched-chain alkynyl group containing from three to six carbon atoms;

or a cycloalkyl group containing three to six carbon atoms;

$R^{21}$ represents:

a halogen atom;

a straight- or branched-chain alkyl group containing up to three carbon atoms optionally substituted by one or more halogen atoms; or a group selected from nitro, cyano, —$S(O)_pR^5$ and —$OR^5$;

q represents two;

m represents two or three; and p represents zero, one or two.

A further preferred class of compounds of formula (I) are those wherein:

$R^1$ represents:

a straight- or branched-chain allyl group containing up to three carbon atoms; or a cycloalkyl group containing three or four carbon atoms optionally substituted by a methyl group;

$R^2$ represents:

a chlorine, bromine or fluorine atom; or a straight- or branched-chain alkyl alkenyl or alkynyl group containing up to four carbon atoms optionally substituted by one or more halogen atoms;

a straight- or branched-chain alkyl group containing up to four carbon atoms which is substituted by a group —$OR^5$; or a group selected from —$COR^5$, —$CO_2R^5$, —$S(O)_pR^6$, —$O(CH_2)_mOR^5$, —$N(R^8)SO_2R^7$ and —$OR^{51}$;

$R^5$ and $R^6$, which may be the same or different, each represents:

a straight- or branched-chain alkyl group containing up to four carbon atoms optionally substituted by one or more chlorine, bromine or fluorine atoms; or a cyclopropyl group;

$R^{51}$ and $R^7$, which may be the same or different, each represents:

a straight- or branched-chain alkyl or alkenyl group containing up to four carbon atoms optionally substituted by one or more chlorine, bromine or fluorine atoms;

a straight- or branched-chain alkynyl group containing three or four carbon atoms; or a cyclopropyl group;

$R^8$ represents:

the hydrogen atom;

a straight- or branched-chain alkyl or alkenyl group containing up to four carbon atoms optionally substituted by one or more chlorine, bromine or fluorine atoms;

a straight- or branched-chain alkynyl group containing three or four carbon atoms; or a cyclopropyl group;

q represents two;

m represents two or three; and p represents zero, one or two.

A further preferred class of compound are those wherein:

$R^1$ represents:

a methyl ethyl, isopropyl, cyclopropyl or 1-methylcyclopropyl group;

$R^2$ represents:

a bromine, chlorine or fluorine atom; or a straight- or branched-chain alkyl or alkenyl group containing up to four carbon atoms optionally substituted by one or more chlorine, bromine or fluorine atoms;

a group selected from —$COR^5$, —$CO_2R^5$, —$SR^6$, —$O(CH_2)_mOR^5$, —$OR^{51}$ and —$N(R^8)SO_2R^7$; or a straight- or branched chain alkyl group containing up to four carbon atoms which is substituted by —$OR^5$;

$R^5$ and $R^6$, which may be the same or different, each represents a straight- or branched-chain alkyl group containing up to three carbon atoms;

$R^{51}$ represents:

a straight- or branched-chain alkyl group containing up to four carbon atoms optionally substituted by one or more chlorine, bromine or fluorine atoms;

a straight- or branched-chain alkenyl or alkynyl group containing three or four carbon atoms; or a cyclopropyl group;

$R^7$ represents:

a straight- or branched-chain alkyl group containing up to three carbon atoms optionally substituted by one or more chlorine, bromine, or fluorine atoms; or an allyl group optionally substituted by one or more chlorine, fluorine or bromine atoms;

$R^8$ represents:

the hydrogen atom;

a straight- or branched-chain alkyl group containing up to three carbon atoms optionally substituted by one or more chlorine, bromine, or fluorine atoms; or an allyl group optionally substituted by one or more chlorine, fluorine or bromine atoms;

q represents two; and m represents two or three.

A further preferred class of compounds of formula (I) are those wherein:

$R^1$ represents cyclopropyl;

$R^2$ represents:

a halogen atom;

$R^7$ represents methyl;

$R^8$ represents hydrogen or methyl; and n represents zero or one.

A further preferred class of compounds of formula (I) are those wherein a group —$XR^3$ is in the 2- or 4-position of the benzoyl ring.

A further preferred class of compounds of formula (I) are those wherein:

R represents hydrogen or —$CO_2Et$;

$R^1$ represents cyclopropyl;

$R^2$ represents a halogen atom or a group selected from nitro, trifluoromethyl, methyl, trifluoromethoxy, —$S(O)_pMe$ and —$N(R^8)SO_2R^7$;

$R^7$ represents a straight- or branched-chain alkyl group containing up to three carbon atoms, phenyl or benzyl;

$R^8$ represents a straight- or branched-chain alkyl group containing up to four carbon atoms, methoxy or phenyl;

p is zero, one or preferably two;

n represents zero, one or two; and q represents two.

Particularly important compounds of formula (I) include the following:

1. 4-[2-chloro-4-(methylsulphonyl)aminobenzoyl]-5-cyclopropylisoxazole;
2. 4-[4-chloro-2-(N-methyl-N-methylsulphonyl)aminobenzoyl]-5-cyclopropylisoxazole;
3. 5-cyclopropyl-4-[2-(N-methyl-N-methylsulphonyl)amino-benzoyl]isoxazole;
4. 4-[4-chloro-2-(N-ethyl-N-methylsulphonyl)aminobenzoyl]-5-cyclopropylisoxazole;
5. 5-cyclopropyl4-[2-(N-methyl-N-methylsulphonyl)amino4-nitro-benzoyl]isoxazole;
6. 5-cyclopropyl-4-[4-(N-methyl-N-methylsulphonyl)amino-2-nitro-benzoyl]isoxazole;
7. 5-cyclopropyl-4-[4-methyl-2-(N-methyl-N-methylsulphonyl)amino-benzoyl]isoxazole;
8. 4-[4-chloro-2-(N-n-propyl-N-methylsulphonyl)aminobenzoyl]-5-cyclopropylisoxazole;
9. 5-cyclopropyl-4-[2-(N-ethyl-N-methylsulphonyl)amino-4-methylsulphonylbenzoyl]isoxazole;

10. 5-cyclopropyl-4-[3,4-dichloro-2-(N-methyl-N-methylsulphonyl)-aminobenzoyl]isoxazole;
11. 5-cyclopropyl-4-[2-(N-methyl-N-methylsulphonyl)amino-4-trifluoromethylbenzoyl]isoxazole;
12. 5-cyclopropyl-4-[2-(N-phenyl-N-methylsulphonyl)amino-benzoyl]isoxazole;
13. 4-[4-bromo-2-(N-methyl-N-methylsulphonyl)aminobenzoyl]-5-cyclopropylisoxazole;
14. 5-cyclopropyl-4-[2-(N-methyl-N-methylsulphonyl)amino-4-methylsulphonylbenzoyl]isoxazole;
15. ethyl 5-cyclopropyl-4-[4-chloro-2-(N-methyl-N-methylsulphonylamino)benzoyl]isoxazole-3-carboxylate;
16. 4-[4-chloro-2-(N-methyl-N-ethylsulphonylamino)benzoyl]-5-cyclopropyl-isoxazole;
17. 5-cyclopropyl-4-[2,4-bis(N-methyl-N-methylsulphonyl)aminobenzoyl]isoxazole;
18. 5-cyclopropyl-4-[2-(N-methyl-N-methylsulphonyl)amino-4-fluorobenzoyl]isoxazole;
19. 4-[2-bromo-4-(N-methyl-N-methylsulphonyl)aminobenzoyl]-5-cyclopropylisoxazole;
20. 4-[2-chloro-4-(N-methyl-N-methylsulphonyl)aminobenzoyl]-5-cyclopropylisoxazole;
21. 4-[3-chloro-2-(N-methyl-N-methylsulphonyl)amino-4-trifluoromethoxybenzoyl]-5-cyclopropylisoxazole;
22. 5-cyclopropyl-4-[2-(N-methyl-N-methylsulphonyl)amino-4-trifluoromethoxybenzoyl]isoxazole;
23. 4-[5-chloro-2-(N-methyl-N-methylsulphonyl)aminobenzoyl]-5-cyclopropylisoxazole;
24. 5-cyclopropyl-4-[2-fluoro-4-(N-methyl-N-methylsulphonyl)aminobenzoyl]isoxazole;
25. 5-cyclopropyl-4-[3,4-difluoro-2-(N-methyl-N-methylsulphonyl)aminobenzoyl]isoxazole;
26. 5-cyclopropyl-4-[4,5-difluoro-2-(N-methyl-N-methylsulphonyl)aminobenzoyl]isoxazole;
27. 5-cyclopropyl-4-[4-iodo-2-(N-methyl-N-methylsulphonyl)aminobenzoyl]isoxazole;
28. 4-[4-chloro-2-(N-isobutyl-N-methylsulphonylaminobenzoyl)]-5-cyclopropylisoxazole;
29. 4-[4-chloro-2-(N-methyl-N-n-propylsulphonyl)aminobenzoyl]-5-cyclopropylisoxazole;
30. 4-[4-chloro-2-(N-methyl-N-phenylsulphonyl)aminobenzoyl]-5-cyclopropylisoxazole;
31. 4-[4-chloro-2-(N-benzylsulphonyl-N-methyl)aminobenzoyl]-5-cyclopropylisoxazole;
32. 4-[4-chloro-2-(N-methyl-N-isopropylsulphonyl)aminobenzoyl]-5-cyclopropylisoxazole;
33. 4-[4-chloro-2-(N-methoxy-N-methylsulphonyl)aminobenzoyl]-5-cyclopropylisoxazole;
34. ethyl 5-cyclopropyl-4-[2-(N-methyl-N-methylsulphonyl)amino-4-trifluoromethylbenzoyl] isoxazole-3-carboxylate.

The numbers 1 to 34 are assigned to these compounds for reference and identification hereinafter.

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) in which R represents hydrogen excluding those wherein a group —XR³ is in the ortho position and X is —NH— may be prepared by the reaction of a compound of formula (II):

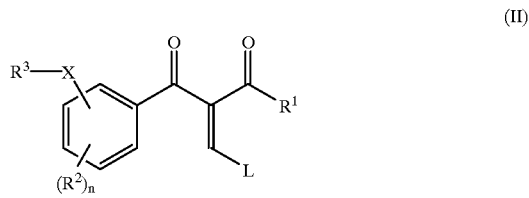

wherein L is a leaving group and $R^1$, $R^2$, $R^3$, n and X are as hereinbefore defined provided that when X is —NH— the group —$XR^3$ is not in the ortho position of the phenyl ring, with hydroxylamine or a salt of hydroxylamine. Hydroxylamine hydrochloride is generally preferred. Generally L is alkoxy, for example ethoxy, or N,N-dialkylamino, for example dimethylamino. The reaction is generally carried out in an organic solvent such as ethanol or acetonitrile or a mixture of a water-miscible organic solvent and water, preferably in a ratio of organic solvent: water of from 1:99 to 99:1, optionally in the presence of a base or acid acceptor such as triethylamine or sodium acetate at a temperature from room temperature to the boiling point of the solvent.

According to a further feature of the present invention compounds of formula (I) in which R represents hydrogen may be prepared by the reaction of a compound of formula (III):

wherein $R^1$ is as hereinbefore defined and Y represents a carboxy group or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran at a temperature from 0° C. to the reflux temperature of the mixture.

According to a further feature of the present invention compounds of formula (I) wherein R represents a group —$CO_2R^4$ excluding those wherein a group —$XR^3$ is in the ortho position and X is —NH— may be prepared by the reaction of a compound of formula (IV)

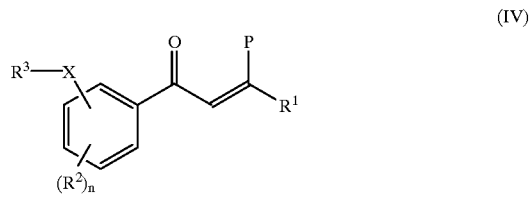

wherein $R^1$, $R^2$, $R^3$, X and n are as hereinbefore defined provided that when X is —NH— the group —$XR^3$ is not in the ortho position of the phenyl ring, and P is a leaving group such as N,N-dialkylamino, with a compound of formula $R^4O_2CC(Z)=NOH$ wherein $R^4$ is as hereinbefore defined and Z is a halogen atom. Generally Z is chlorine or bromine. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula I in which R represents a group —$CO_2R^4$ excluding those wherein a group —$XR^3$ is in the ortho position and X is —NH— may be prepared by the reaction of a compound of formula (V):

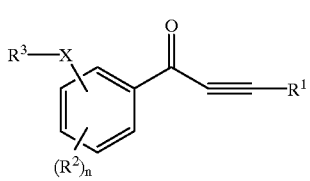

(V)

wherein $R^1$, $R^2$, $R^3$, X and n are as hereinbefore defined provided that when X is —NH— the group —$XR^3$ is not in the ortho position of the phenyl ring, with a compound of formula $R^4O_2CC(Z)=NOH$ wherein Z and $R^4$ are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula (I) wherein R represents —$CO_2R^4$ excluding those wherein a group —$XR^3$ is in the ortho position of the phenyl ring and X is —NH— may be prepared by the reaction of a salt of compounds of formula (VI):

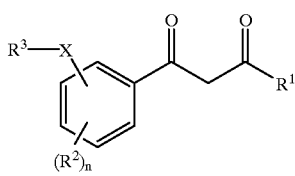

(VI)

wherein $R^1$, $R^2$, $R^3$, X and n are as hereinbefore defined provided that when X is —NH— the group —$XR^3$ is not in the ortho position of the phenyl ring, with a compound of formula $R^4O_2CC(Z)=NOH$ wherein $R^4$ and Z are as hereinbefore defined. Preferred salts include sodium or magnesium salts. The reaction may be performed in an inert solvent such as dichloromethane or acetonitrile at a temperature between room temperature and the reflux temperature of the mixture. The salt of a compound of formula (VI) is generally prepared in situ by treating the compound of formula (VI) with a base. Examples of suitable bases include alkaline earth metal alkoxides such as magnesium methoxide.

According to a further feature of the present invention compounds of formula (I) in which X represents —NH— may be prepared by the deprotection of a compound of formula (VII):

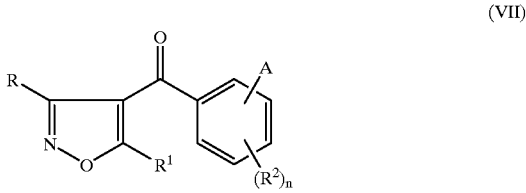

(VII)

wherein R, $R^1$, $R^2$ and n are as hereinbefore defined and A represents —$NX^1R^3$ wherein $R^3$ is as hereinbefore defined and $X^1$ represents a protecting group which can be removed under acidic or neutral reaction conditions. The protecting group may be for example a benzyl group (which may be removed by hydrogenolysis) or a t-butyloxycarbonyl group (t-BOC). Suitable methods of protection and deprotection are described in the literature (for example in "Protective Groups in Organic Synthesis", by T. W. Greene and P. G. M. Wuts). The intermediates of formula (VII) are novel and as such constitute a further feature of the present invention.

Intermediates in the preparation of compounds of formula (I) may be prepared by the application or adaptation of known methods.

Compounds of formula (II) may be prepared by the reaction of compounds of formula (VI) with either a trialkyl orthoformate such as triethyl orthoformate or a dimethylformamide dialkyl acetal such as dimethylformamide dimethyl acetal.

The reaction with a trialkyl orthoformate can be carried out in the presence of acetic anhydride at the reflux temperature of the mixture and the reaction with dialkylformamide dialkyl acetal is carried out optionally in the presence of an inert solvent at a temperature from room temperature to the reflux temperature of the mixture.

Compounds of formula (IV) may be prepared by the reaction of a compound of formula (VIII) with a benzoyl chloride of formula (IX):

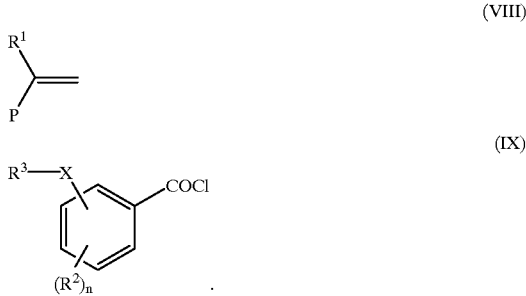

(VIII)

(IX)

The reaction is generally carried out in the presence of an organic base such as triethylamine in an inert solvent such as toluene or dichloromethane at a temperature between −20° C. and room temperature.

Compounds of formula (V) may be prepared by the metallation of the appropriate acetylene of formula (X):

$R^1C\equiv CH$  (X)

followed by reaction of the metal salt thus obtained with a benzoyl chloride of formula (IX). The metallation is generally performed using n-butyl lithium in an inert solvent such as ether or tetrahydrofuran at a temperature from −78° C. to 0° C. The subsequent reaction with the benzoyl chloride is carried out in the same solvent at a temperature between −78° C. and room temperature.

Compounds of formula (VI) may be prepared by the reaction of an acid chloride of formula (IX) with the metal salt of a compound of formula (XI):

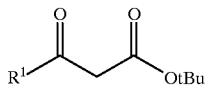

(XI)

wherein $R^1$ is as hereinbefore defined, to give a compound of formula (XII):

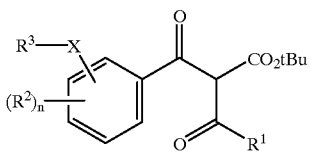

(XII)

wherein $R^1$, $R^2$ $R^3$, X and n are as hereinbefore defined, which is subsequently decarboxylated to give a compound of formula (VI). Generally the reaction to produce the compound of formula (XII) is performed in a solvent such as a lower alcohol, preferably methanol, in the presence of a metal, preferably magnesium. The reaction may also be performed using a pre-prepared metal salt of a compound of formula (XI). The decarboxylation is generally performed by refluxing the compound of formula (XII) in the presence of a catalyst, such as paratoluenesulphonic acid or trifluoroacetic acid, in an inert solvent e.g. toluene or 1,2-dichloroethane.

Compounds of formula (VII) may be prepared by the processes hereinbefore described for preparing compounds of formula (I) in which R, $R^1$, $R^2$ and n are as hereinbefore defined and the group —$XR^3$ is replaced by the group A.

Acid chlorides of formula (IX) may be prepared by the reaction of a benzoic acid of formula (XIII):

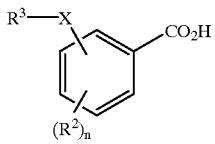

(XIII)

with a chlorinating agent, for example thionyl chloride at the reflux temperature of the mixture. In some cases the benzoyl chlorides may also be prepared by reaction of the benzoic acid with oxalyl chloride in a solvent such as 1,2-dichloroethane at from ambient to reflux temperature.

A number of the benzoic acids of formula (XIII) are novel and as such constitute a further feature of the present invention. Compounds of formula (XIII) in which $R^2$ represents a chlorine, bromine or iodine atom or a group selected from nitro, trifluoromethyl, methyl, trifluoromethoxy, —SMe, —SOMe, $SO_2Me$ and —$N(R^8)$ $SO_2R^7$; $R^7$ represents a straight- or branched-chain alkyl group containing up to three carbon atoms, phenyl or benzyl; $R^8$ represents a straight- or branched-chain allyl group containing up to four carbon atoms, methoxy or phenyl; and q represents two, are especially preferred.

Compounds of formula (XIII) in which $R^3$ represents —$SO_2R^7$ may be prepared by the hydrolysis of the corresponding ester of formula (XIV):

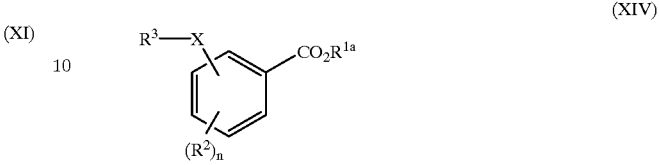

(XIV)

wherein $R^{1a}$ is an alkyl group and X is —$NR^8$—. The reaction is generally carried out in the presence of a base (e.g. sodium hydroxide or lithium hydroxide) in a solvent such as an aqueous alcohol (e.g. ethanol) at a temperature from room temperature to reflux.

Esters of formula (XIV) in which $R^8$ is not hydrogen may be prepared by the reaction of the corresponding compound of formula (XIV) in which $R^8$ is hydrogen with a compound of formula $R^8$—$L^1$, wherein $R^8$ is as hereinbefore defined excluding hydrogen and $L^1$ is a leaving group in the presence of a base. The reaction is particularly useful for producing esters of formula (XIV) in which $R^8$ is alky. Generally $L^1$ is halogen (preferably iodine) or —OH and the base is potassium carbonate. The reaction is performed at a temperature from room temperature to reflux in an inert solvent, preferably acetone.

Esters of formula (XIV) in which $R^8$ is the same as $R^{1a}$ may also be prepared from compounds of formula (XIII) in which $R^3$ is —$SO_2R^7$ and $R^8$ is hydrogen by reaction with a compound of formula $R^{1a}$—$L^1$, as described in the above reaction. Where L is OH optionally a mixture of thionyl chloride with $R^{1a}$—OH may be used.

Esters of formula (XIV) in which $R^8$ is the hydrogen atom may also be prepared by the reaction of a compound of formula (XIII) in which $R^8$ is hydrogen with a compound of formula $R^{1a}$—OH. The reaction is performed in the presence of a strong acid (preferably concentrated sulphuric acid) optionally using the alcohol of formula $R^{1a}$—OH as solvent, at a temperature from ambient to reflux.

Compounds of formula (XIII) in which $R^3$ represents —$SO_2R^7$ and X is —NH— may also be prepared by the hydrolysis of a compound of formula (XV):

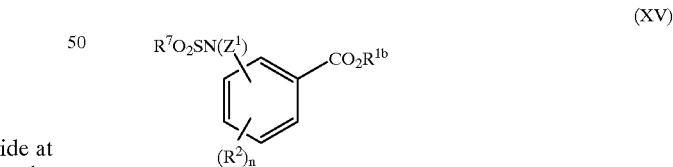

(XV)

wherein $Z^1$ is hydrogen or —$SO_2R^7$, $R^{1b}$ is alkyl or hydrogen and at least one of $R^{1b}$ and $Z^1$ is not hydrogen, using a base. Preferably sodium hydroxide or lithium hydroxide is used and the reaction is conveniently performed in a solvent such as aqueous ethanol at a temperature from room temperature to reflux.

Compounds of formula (XV) in which $Z^1$ is hydrogen and $R^{1b}$ is alkyl may be prepared by the hydrolysis of the corresponding compound of formula (XV) in which $Z^1$ is —$SO_2R^7$ by the same procedure described above for the preparation of a compound of formula (XIII) from a compound of formula (XV) wherein the reaction is performed for a shorter period (to prevent hydrolysis of the ester group —$CO_2R^{1b}$).

Compounds of formula (XV) in which $Z^1$ is hydrogen may be prepared by the sulphonation of an aniline of formula (XVI):

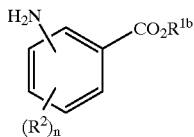

(XVI)

using a compound of formula $R^7SO_2Cl$ in the presence of a base. Preferably the base used is triethylamine and the reaction is performed in an inert solvent (e.g. dichloromethane or acetonitrile) at a temperature from 0° C. to reflux. Compounds of formula (XV) in which $Z^1$ is —$SO_2R^7$ may also be prepared by this method, using an excess of compound of formula $R^7SO_2Cl$.

Compounds of formula (XIII) in which the group —$XR^3$ is ortho to the acid group and $R^3$ is —$SO_2R^7$ may be prepared by the reaction of a compound of formula (XVII):

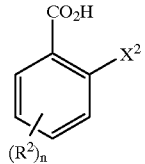

(XVII)

wherein $X^2$ is chlorine or preferably bromine or iodine, with a compound of formula $R^8NHSO_2R^7$ in the presence of a strong base. Generally the reaction is performed in the presence of a catalyst e.g. copper (I) chloride or preferably copper (I) bromide or iodide, in an inert solvent such as dioxan or toluene. The preferred strong base is sodium hydride and the reaction is conveniently performed at a temperature from 50° C. to reflux.

Compounds of formula (XIII) in which the group $XR^3$ is ortho to the acid group, $R^3$ is —$SO_2R^7$ and n is zero may be prepared by the reaction of a salt of formula (XVIII):

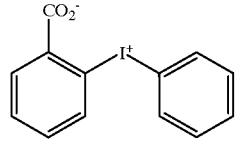

(XVIII)

with a compound of formula $R^8NHSO_2R^7$ in the presence of a strong base (e.g. sodium hydride) and a catalyst (e.g. copper acetate). The reaction is typically performed in an inert solvent, preferably dimethoxyethane according to the methods described by R. A. Scherrer and H. R. Beatty (J. Org. Chem., Vol. 45, p2127, 1980).

Intermediates of formula (III), (V), (VIII), (X), (XI), (XIV), (XV), (XVI), (XVII) and (XVIII) are known or may be prepared by the application or adaptation of known methods.

Those skilled in the art will appreciate that some compounds of formula (I) may be prepared by the interconversion of other compounds of formula (I) and such interconversions constitute yet more features of the present invention. Examples of such interconversions are hereafter described.

According to a further feature of the present invention compounds in which p is one or two and/or q is two may be prepared by the oxidation of the sulphur atom of the corresponding compounds in which p is 0 or 1 and/or q is zero. The oxidation of the sulphur atom is generally carried out using for example 3-chloroperoxybenzoic acid in an inert solvent such as dichloromethane at a temperature from −40° C. to room temperature.

The following examples illustrate the preparation of compounds of formula (I) and the following reference examples illustrate the preparation of intermediates of the invention. In the present specification b.p. means boiling point; m.p. means melting point; cPr represents cyclopropyl.

EXAMPLE 1

Hydroxylamine hydrochloride (0.53 g) was added to a stirred solution of 1-[2-chloro-4-(methylsulphonylamino) phenyl]-3-cyclopropyl-2-ethoxymethylenepropane-1,3-dione (2.8 g) in ethanol. Sodium acetate (0.63 g) was then added portionwise over a period of ten minutes. The mixture was then stirred at room temperature for 0.5 hours. Further quantities of hydroxylamine hydrochloride (0.2 g) and sodium acetate (0.24 g) were added and stirring was continued for 0.5 hours. Water was added, the mixture was extracted with dichloromethane and the combined organic extracts were washed with water, dried and the solvent evaporated. The crude product was purified by column chromatography to yield 4-[2-chloro-4-(methylsulphonylamino)benzoyl]-5-cyclopropylisoxazole (compound 1) as a white solid, 1.66 g, m.p. 122.8–124.5° C.

By proceeding in a similar manner, the following compounds of formula I were prepared:

| Cpd. | Name | m.p./NMR |
|---|---|---|
| 2 | 4-[4-chloro-2-(N-methyl-N-methylsulphonyl)aminobenzoyl]-5-cyclopropylisoxazole | 128.3–130.8° C. |
| 3 | 5-cyclopropyl-4-[2-(N-methyl-N-methylsulphonyl)aminobenzoyl]isoxazole | 110.8–113.8° C. |
| 11 | 5-cyclopropyl-4-[2-(N-methyl-N-methylsulphonyl)amino-4-trifluoromethyl-benzoyl]isoxazole | (a) |
| 21 | 4-[3-chloro-2-(N-methyl-N-methylsulphonyl)amino-4-trifluoromethoxy]benzoyl-5-cyclopropylisoxazole | (b) |
| 22 | 5-cyclopropyl-4-[2-(N-methyl-N-methylsulphonyl)amino-4-trifluoromethoxy]benzoyl-isoxazole | (c) |
| 23 | 4-[5-chloro-2-(N-methyl-N-methylsulphonyl)amino]-benzoyl-5-cyclopropylisoxazole | 111–113° C. |

(a) NMR(CDCl$_3$): 1.2–1.5(m, 4H), 2.65(m, 1H), 2.95(s, 3H), 3.3(s, 3H), 7.6(dd, 1H), 7.75(m, 2H), 8.2(s, 1H).
(b) NMR(CDCl$_3$): 1.15(m, 2H), 1.25(m, 2H), 2.6(m, 1H), 2.9(s, 3H), 3.3 (s, 3H), 7.35(m, 2H), 8.15(s, 1H).
(c) NMR(CDCl$_3$): 1.15(m, 2H), 1.25(m, 2H), 2.6(m, 1H), 2.9(s, 3H), 3.2 (s, 3H), 7.2(m, 2H), 7.5(d, 1H), 8.1(s, 1H).

EXAMPLE 2

Hydroxylamine hydrochloride (0.76 g) was added to a mixture of 1-[4-chloro-2-(N-ethyl-N-methylsulphonylamino)phenyl]-3-cyclopropyl-2-dimethylaminomethylenepropan-1,3-dione (3.83 g) in ethanol. The mixture was stirred for 1 hour and evaporated to dryness. The residue was dissolved in dichloromethane and washed with water, dried (magnesium sulphate) and filtered. The filtrate was evaporated to dryness and the residue was purified by chromatography eluted with a mixture of cyclohexane, dichloromethane and ethyl acetate. The product was triturated with a mixture of ether and hexane and filtered to give 4-[4-chloro-2-(N-ethyl-N-methylsulphonylamino)benzoyl]-5-cyclopropylisoxazole (compound 4, 0.81 g) as a white solid, mp. 114–115.8° C.

By proceeding in a similar manner the following compounds of formula (I) were prepared from the appropriately substituted starting materials.

| Cpd | R | $R^1$ | X—$R^3$ | $(R^2)_n$ | m. p. (° C.) NMR |
|---|---|---|---|---|---|
| 5 | H | cPr | 2-N(Me)SO$_2$Me | 4-NO$_2$ | 113–115 |
| 6 | H | cPr | 4-N(Me)SO$_2$Me | 2-NO$_2$ | 116–117 |
| 7 | H | cPr | 2-N(Me)SO$_2$Me | 4-Me | 120–122 |
| 8 | H | cPr | 2-N(nPr)SO$_2$Me | 4-Cl | 127–128 |
| 9 | H | cPr | 2-N(Et)SO$_2$Me | 4-SO$_2$Me | 171–172 |
| 10 | H | cPr | 2-N(Me)SO$_2$Me | 3,4-Cl$_2$ | 153–154 |
| 12 | H | cPr | 2-N(Ph)SO$_2$Me | — | 114–115 |
| 13 | H | cPr | 2-N(Me)SO$_2$Me | 4-Br | 128–130 |
| 14 | H | cPr | 2-N(Me)SO$_2$Me | 4-SO$_2$Me | 130–132 |
| 16 | H | cPr | 2-N(Me)SO$_2$Et | 4-Cl | 77.5–78.5 |
| 17 | H | cPr | 2-N(Me)SO$_2$Me | 4-N(Me)SO$_2$Me | 74–76 |
| 18 | H | cPr | 2-N(Me)SO$_2$Me | 4-F | 154–155 |
| 19 | H | cPr | 4-N(Me)SO$_2$Me | 2-Br | 84–85 |
| 20 | H | cPr | 4-N(Me)SO$_2$Me | 2-Cl | 92.4–94.2 |
| 24 | H | cPr | 4-N(Me)SO$_2$Me | 2-F | 103–104 |
| 25 | H | cPr | 2-N(Me)SO$_2$Me | 3,4-diF | 134–136 |
| 26 | H | cPr | 2-N(Me)SO$_2$Me | 4,5-diF | 140–143 |
| 27 | H | cPr | 2-N(Me)SO$_2$Me | 4-I | 128–129 |
| 28 | H | cPr | 2-N(iBu)SO$_2$Me | 4-Cl | 118–118.5 |
| 29 | H | cPr | 2-N(Me)SO$_2$nPr | 4-Cl | 112–113 |
| 30 | H | cPr | 2-N(Me)SO$_2$Ph | 4-Cl | (a) |
| 31 | H | cPr | 2-N-(Me)SO$_2$Bz | 4-Cl | (b) |
| 32 | H | cPr | 2-N(Me)SO$_2$iPr | 4-Cl | 130–132 |
| 33 | H | cPr | 2-N(OMe)SO$_2$Me | 4-Cl | 85–87 |

Note that Ph represents phenyl; Bz represents benzyl.
(a) NMR(CDCl$_3$) 1.15(m, 2H), 1.3(m, 2H), 2.65(m, 1H), 3.15(s, 3H), 6.8 (d, 1H), 7.48(m, 7H), 8.1(s, 1H).
(b) NMR(CDCl$_3$) 1.15(m, 2H), 1.3(m, 2H), 2.6(m, 1H), 3.1(s, 3H), 4.25(s, 2H), 6.9(d, 1H), 7.3(m, 7H). 8.15(s, 1H).

EXAMPLE 3

1-[4-Chloro-2-(N-methyl-N-methylsulphonyl)aminophenyl]-3-cyclopropylpropan-1,3-dione (3.8 g) and magnesium turnings (0.3 g) were stirred at room temperature in anhydrous methanol. Reaction was initiated by adding carbon tetrachloride (3 ml) and the resulting solution was stirred at room temperature for a further 0.5 hours and evaporated to dryness. Toluene was added and the solution was re-evaporated to give a brown solid which was suspended with stirring in dry acetonitrile. The suspension was heated to 65° C. and a solution of ethyl chloroximidoacetate (2.6 g) in dry acetonitrile was added dropwise over one hour. The resulting suspension was stirred at 65° C. for a further 2 hours, then cooled to about 40° C. Dilute hydrochloric acid (2N) was added with stirring, the resulting layers were separated and the aqueous layer was extracted with ethyl acetate. The organic phases were combined, washed with brine, dried (sodium sulphate) and evaporated to give an orange oil which was crystallised from diethyl ether to yield ethyl 4-[4-chloro-2-(N-methyl-N-methylsulphonyl) aminobenzoyl]-5-cyclopropylisoxazole-3-carboxylate (compound 15, 2.8 g) as a beige solid, m.p. 134–135.6° C.

By proceeding in a similar manner ethyl 5-cyclopropyl-4-[2-(N-methyl-N-methylsulphonyl)amino-4-trifluoromethyl]benzoylisoxazole-3-carboxylate, compound 34 was prepared, m.p. 98–99.5° C.

Reference Example 1

A solution of 3-cyclopropyl-1-[2-(N-methyl-N-methylsulphonyl)amino4trifluoromethylphenyl]propan-1,3-dione (4.21 g) and triethylorthoformate (3.44 g) in acetic anhydride was stirred at reflux temperature for 3.5 hours and then at room temperature overnight. Excess solvents were removed by evaporation and remaining traces of solvent were removed by azeotropic evaporation with toluene to yield 3-cyclopropyl-2-ethoxymethylene-1-[2-(N-methyl-N-methylsulphonyl)amino-4-trifluoromethylphenyl]propan-1, 3-dione as a brown oil (4.9 g).

By proceeding in a similar manner the following compounds were prepared from the appropriately substituted starting materials:

| $R^1$ | -X-$R^3$ | $(R^2)_n$ |
|---|---|---|
| cPr | 4-NHSO$_2$Me | 2-Cl |
| cPr | 4-N(Me)SO$_2$Me | 4-Cl |
| cPr | 2-N(Me)SO$_2$Me | 3-Cl-4-OCF$_3$ |
| cPr | 2-N(Me)SO$_2$Me | 4-OCF$_3$ |
| cPr | 2-N(Me)SO$_2$Me | 5-Cl |
| cPr | 2-N(Me)SO$_2$Me | — |

Reference Example 2

A mixture of 1-[4-chloro-2-(N-ethyl-N-methylsulphonylamino)phenyl]-3-cyclopropylpropan-1,3-dione (3.5 g) and dimethylformamide dimethyl acetal (1.5 ml) in dichloromethane was stirred at room temperature overnight and heated at reflux for 3 days. After cooling the mixture was evaporated to dryness to give 1-[4-chloro-2-(N-ethyl-N-methylsulphonylaminophenyl]-3-cyclopropyl-2-dimethylaminomethylenepropan-1,3-dione (3.83 g) as an orange gum which was not purified further.

By proceeding in a similar manner the following compounds were prepared from the appropriately substituted starting materials.

| $R^1$ | X-$R^3$ | $(R^2)_n$ |
|---|---|---|
| cPr | 2-N(Me)SO$_2$Me | 4-NO$_2$ |
| cPr | 4-N(Me)SO$_2$Me | 2-Cl |
| cPr | 4-N(Me)SO$_2$Me | 2-NO$_2$ |
| cPr | 2-N(Me)SO$_2$Me | 4-Me |

-continued $$R^3-X-\text{(aryl, with } (R^2)_n\text{)}-C(O)-C(=CHNMe_2)-C(O)-R^1$$

| R¹ | X-R³ | (R²)ₙ |
|---|---|---|
| cPr | 2-N(nPr)SO₂Me | 4-Cl |
| cPr | 2-N(Et)SO₂Me | 4-SO₂Me |
| cPr | 2-N(Me)SO₂Me | 3,4-Cl₂ |
| cPr | 2-N(Ph)SO₂Me | — |
| cPr | 2-N(Me)SO₂Me | 4-SO₂Me |
| cPr | 2-N(Me)SO₂Me | 4-Br |
| cPr | 2-N(Me)SO₂Et | 4-Cl |
| cPr | 2-N(Me)SO₂Me | 4-N(Me)SO₂Me |
| cPr | 2-N(Me)SO₂Me | 4-F |
| cPr | 4-N(Me)SO₂Me | 2-Br |
| cPr | 4-N(Me)SO₂Me | 2-Cl |
| cPr | 4-N(Me)SO₂Me | 2-F |
| cPr | 2-N(Me)SO₂Me | 3,4-F₂ |
| cPr | 2-N(Me)SO₂Me | 4,5-F₂ |
| cPr | 2-N(Me)SO₂Me | 4-I |
| cPr | 2-N(isobutyl)SO₂Me | 4-Cl |
| cPr | 2-N(Me)SO₂nPr | 4-Cl |
| cPr | 2-N(Me)SO₂Ph | 4-Cl |
| cPr | 2-N(Me)SO₂Bz | 4-Cl |
| cPr | 2-N(Me)SO₂iPr | 4-Cl |
| cPr | 2-N(OMe)SO₂Me | 4-Cl |

Reference Example 3

A suspension of magnesium (0.47 g) in methanol was warmed gently to initiate reaction and then heated at reflux until all of the magnesium had dissolved. It was cooled slightly and t-butyl 3-cyclopropyl-3-oxopropionate (2.39 g) was added. The mixture was stirred and heated at reflux for 25 minutes then evaporated to dryness. It was dissolved in toluene and re-evaporated to dryness. The residue was again dissolved in toluene and 2-chloro-4-(methylsulphonylamino)benzoyl chloride (3.2 g) was added. The mixture was stirred at room temperature overnight. Hydrochloric acid (2M) was added and the mixture was stirred. The layers were separated and the organic layer was dried (magnesium sulphate) and filtered. The filtrate was evaporated to give t-butyl 2-[2-chloro-4-(methylsulphonylamino)benzoyl]-3-cyclopropyl-3-oxopropionate (3.7 g) as a white solid, m.p. 137–140° C.

t-Butyl 2-[2-chloro-4-(methylsulphonylamino)benzoyl]-3-cyclopropyl-3-oxopropionate (2 g) was dissolved in toluene and p-toluenesulphonic acid (0.2 g) was added. The mixture was stirred and heated at reflux for 0.5 hours. It was cooled, washed with water, dried (magnesium sulphate) and filtered. The filtrate was evaporated to dryness to give 1-[2-chloro-4-(methylsulphonylamino)phenyl]-3-cyclopropylpropan-1,3-dione (1.48 g) as a white solid, m.p. 119.9–121.6° C.

By proceeding in a similar manner the following compounds of formula (VI) above were prepared from the appropriately substituted starting materials without isolation of the intermediate ester.

| R | X—R³ | (R²)ₙ | m. p. (° C.) or NMR |
|---|---|---|---|
| cPr | 2-N(Me)SO₂Me | 4-Cl | 93.3–96.5 |
| cPr | 2-N(Me)SO₂Me | 4-NO₂ | — |
| cPr | 2-N(Et)SO₂Me | 4-Cl | a |
| cPr | 4-N(Me)SO₂Me | 2-Cl | — |
| cPr | 4-N(Me)SO₂Me | 2-NO₂ | — |
| cPr | 2-N(Me)SO₂Me | 4-Me | b |
| cPr | 2-N(nPr)SO₂Me | 4-Cl | c |
| cPr | 2-N(Et)SO₂Me | 4-SO₂Me | d |
| cPr | 2-N(Me)SO₂Me | 3,4-Cl₂ | — |
| cPr | 2-N(Ph)SO₂Me | | e |
| cPr | 2-N(Me)SO₂Me | 4-CF₃ | — |
| cPr | 2-N(Me)SO₂Me | 4-N(Me)SO₂Me | f |
| cPr | 2-N(Me)SO₂Et | 4-F | g |
| cPr | 2-N(nPr)SO₂Me | 2-Cl | — |
| cPr | 2-N(Me)SO₂Me | 4-SO₂Me | h |
| cPr | 2-N(Me)SO₂Me | 3-Cl-4-OCF₃ | i |
| cPr | 2-N(Me)SO₂Me | 4-OCF₃ | j |
| cPr | 2-N(Me)SO₂Me | 5-Cl | k |
| cPr | 2-N(Me)SO₂Me | 4,5-F₂ | 104–105 |
| cPr | 2-N(Me)SO₂Me | 4-I | 131.5–134 |
| cPr | 2-N(Me)SO₂Me | — | 110–113 |

Note:
a NMR(CDCl₃)0.9–1.4(m, 7H)1.7–1.9(m, 1H)3.0(s, 3H)3.65(q, 2H)6.1(s, 1H)7.4(m, 2H)7.55(d, 1H)16.0–16.3(bs, 1H).
b NMR(CDCl₃)0.9–1.1(m, 2H)1.15–1.25(m, 2H)1.7–1.85(m, 1H)2.35(s, 3H)2.95(s, 3H)3.25(s, 3H)6.1(s, 1H)7.15(d, 1H)7.2(s, 1H)7.5(d, 1H)16.1–16.3(bs, 1H).
c NMR(CDCl₃)0.9(t, 3H)1.05(m, 2H)1.25(m, 2H)1.45—11.65(m, 4H)1.78(m, 1H)3.03(s, 3H)6.15(s, 1H)7.38–7.48(m, 2H)7.57(dd, 1H)16.12(0.5H, bs).
d NMR(CDCl₃)1.0–1.3(m, 7H)1.79(m, 1H)3.00(s, 3H)3.06(s, 3H)6.15(s, 1H)7.78(d, 1H)7.98(m, 2H).
e NMR(CDCl₃)0.88(m, 2H)1.06(m, 2H)1.58(m, 1H)3.0(s, 3H)5.82(s, 1H)7.0–7.6(m, 9H).
f NMR(CDCl₃)1.05(m, 2H)1.23(m, 2H)1.78(m, 1H)2.9(s, 3H)2.98(s, 3H)3.28(s, 3H)3.33(s, 3H)6.15(s, 1H)7.43(dd, 1H)7.5(d, 1H)7.66(d, 1H).
g NMR(CDCl₃)1.0(m, 2H)1.18(m, 2H)1.72(m, 1H)2.96(s, 3H)3.2(s, 3H)6.07(s, 1H)7.0–7.2(m, 2H)16.1(bs, 0.5H).
h NMR(CDCl₃)1.0(m, 2H)1.18(m, 2H)1.72(m, 1H)2.9(s, 3H)3.05(s, 3H)3.24(s, 3H)6.07(s, 2H)7.71(d, 1H)7.9(m, 1H)7.97(d, 1H).
i NMR(CDCl₃)0.9(m, 2H)1.1(m, 2H)1.65(m, 1H)2.9(s, 3H)3.25(s, 3H)6.0(s, 1H)7.35(m, 1H)7.45(d, 1H)16.0(brs, 1H).
j NMR(CDCl₃)1.0(m, 2H)1.2(m, 1H)1.7(m, 1H)3.0(s, 3H)3.25(s, 3H)6.05(s, 1H)7.25(m, 2H)7.6(d, 1H)16.0(s, 1H).
k NMR(CDCl₃)0.9(m, 2H)1.1(m, 2H)1.65(m, 1H)2.9(s, 3H)3.2(s, 3H)6.0(s, 1H)7.35(m, 2H)7.5(d, 1H)16.0(brs, 1H).

Reference Example 4

For the following diketones of formula (VI) an alternative decarboxylation method was used, the corresponding t-butyl 2-aroyl-3-cyclopropyl-3-oxopropionate being prepared as described above. t-Butyl 2-[4-chloro-2-(N-ethylsulphonyl-N-methyl)aminobenzoyl]-3-cyclopropyl-3-oxopropionate was dissolved in 1,2-dichloroethane. The solution was stirred and trifluoroacetic acid (1.5 equivalent) was added. The mixture was stirred at room temperature for 3 hours then evaporated to dryness. The residue was purified by column chromatography (ethyl acetate/cyclohexane/dichloromethane) to yield 1-[4-chloro-2-(N-ethylsulphonyl-N-methyl)aminophenyl]-3-cyclopropylpropan-1,3-dione (6.79 g) as a red oil, NMR (CDCl3) 1.05 (m,2H), 1.2(m,2H), 1.41(t,3H), 1.77(m,1H), 3.16(q,2H), 3.28(s,3H), 6.1(s,1H), 7.4(dd,1H), 7.47(d,1H), 7.65(d,1H), 16.05(bs,0.5H).

By proceeding in a similar manner the following compounds of formula (VI) above were prepared from the appropriately substituted starting materials:
1-[4bromo-2-(N-methyl-N-methylsulphonyl)aminophenyl]-3-cyclopropylpropan-1,3-dione, m.p. 120–122° C.;
1-[2-bromo-4-(N-methyl-N-methylsulphonyl)aminophenyl]-3-cyclopropylpropan-1,3-dione, NMR (CDCl3) 1.03(m,2H), 1.23(m,2H), 1.77(m,₁H), 2.9(s,3H), 3.37(s,3H), 6.08(s,1H), 7.45(dd,1H), 7.58(d,1H), 7.67(d, 1H), 15.87(bs,0.5H);

1-cyclopropyl-3-[2-fluoro-4-(N-methyl-N-methylsulphonyl)-aminophenyl]-propan-1,3-dione as a yellow solid (using toluene as the solvent in place of 1,2-dichloroethane);

1-cyclopropyl-3-[2-(N-methyl-N-methylsulphonyl)amino-4-trifluoromethylphenyl]propan-1,3-dione as a brown gum (using dichloromethane as the solvent in place of 1,2-dichloroethane);

1-[4-chloro-2-(N-methyl-N-propylsulphonyl) aminophenyl]-3-cyclopropylpropan-1,3-dione.

Benzoyl chlorides were prepared by heating the appropriately substituted benzoic acids with thionyl chloride. The excess thionyl chloride was removed by evaporation the benzoyl chlorides thus obtained were used without further purification. In some cases the benzoyl chlorides were prepared by reaction of the benzoic acid with oxalyl chloride in 1,2-dichloroethane at ambient temperature. Evaporation of the solvents in vacuo gave the corresponding benzoyl chlorides.

Reference Example 5

2N Sodium hydroxide solution (20 ml) was added to a stirred solution of methyl 4-chloro-2-(N-methyl-N-methylsulphonylamino)benzoate (2.75 g) in methanol. The mixture was stirred at reflux for 0.5 hours. After cooling, the mixture was acidified with 2N hydrochloric acid and extracted with ethyl acetate. The organic extracts were combined, dried and evaporated to yield 4-chloro-2-(N-methyl-N-methylsulphonylamino)benzoic acid as a white solid (2.45 g), m.p. 161–164° C.

By proceeding in a similar manner, the following compounds were prepared:

2-(N-methyl-N-methylsulphonylamino)-4nitrobenzoic acid NMR (DMSO-$d_6$) 3.1(s,3H) 3.3(s,3H) 7.95(d1H) 8.3(d, 1H) 8.4(s,1H) 13.3–13.8(bs,1H);

4-chloro-2-(N-ethyl-N-methylsulphonylamino)benzoic acid m.p. 148–151° C.;

2-chloro-4-(N-methyl-N-methylsulphonylamino)benzoic acid m.p.152–153° C.;

4-(N-methyl-N-methylsulphonylamino)-2-nitrobenzoic acid m.p. 177–178.6° C.;

4-methyl-2-(N-methyl-N-methylsulphonylamino)benzoic acid m.p. 185–187° C.;

4-chloro-2-(N-methylsulphonyl-N-propyl)aminobenzoic acid, m.p. 133–135° C.;

3,4-dichloro-2-(N-methyl-N-methylsulphonyl) aminobenzoic acid, m.p. 118–119.4° C.;

2-(N-methyl-N-methylsulphonyl)amino-4-trifluoromethylbenzoic acid, m.p. 157–160° C.;

4-bromo-2-(N-methyl-N-methylsulphonyl)aminobenzoic acid, m.p. 181–182° C.;

4-chloro-2-(N-ethylsulphonyl-N-methyl)aminobenzoic acid, m.p. 132–134° C.;

2-bromo-4-(N-methyl-N-methylsulphonyl)aminobenzoic acid, m.p. 153.5–155.5° C.;

2,4-bis(N-methyl-N-methylsulphonyl)aminobenzoic acid, NMR (CDCl$_3$); 2.8 (s,3H), 2.9(s,3H), 3.23(s,3H), 3.3(s, 3H), 7.4(dd,1H), 7.48(d,1H), 8.03(d,1H);

4-fluoro-2-(N-methyl-N-methylsulphonyl)aminobenzoic acid, NMR (CDCl$_3$); 3.06(s,3H), 3.28(s,3H), 7.1–7.3(m, 2H), 8.1(m,1H);

2-fluoro-4-(N-methyl-N-methylsulphonyl)aminobenzoic acid, m.p. 189–191° C.;

3,4-difluoro-2-(N-methyl-N-methylsulphonyl) aminobenzoic acid, m.p. 159.5–161° C.;

3-chloro-2-(N-methyl-N-methylsulphonyl)amino-4-trifluoromethoxybenzoic acid, NMR(CDCl$_3$) 3.0(s,3H), 3.3(s,3H), 6.7 (brs,1H), 7.4(m,1H), 8.0(d,1H);

2-(N-methyl-N-methylsulphonyl)amino-4-trifluoromethoxybenzoic acid, m.p. 138.5–141° C.;

5-chloro-2-(N-methyl-N-methylsulphonyl)aminobenzoic acid, NMR(DMSOd$_6$) 3.0(s,3H), 3.2(s,3H), 7.6(d,1H), 7.65(m,1H), 7.75(m,1H);

4-chloro-2-(N-isobutyl-N-methylsulphonyl)aminobenzoic acid, m.p. 158–159° C.;

4-chloro-2-(N-methyl-N-propylsulphonyl)aminobenzoic acid, m.p. 143.5–144.5° C.;

4-chloro-2-(N-methyl-N-phenylsulphonyl)aminobenzoic acid, m.p. 180–181° C.;

4-chloro-2-(N-benzylsulphonyl-N-methyl)aminobenzoic acid, m.p. 180–185° C.

2-(N-methyl-N-methylsulphonyl)aminobenzoic acid, m.p. 146–149° C.

Reference Example 6

Potassium carbonate (12.5 g) was added to a stirred solution of methyl 4-chloro-2-(N-methylsulphonylamino) benzoate (7.5 g) in acetone. The mixture was stirred for 15 minutes and methyl iodide (8.0 g) was added. The resultant mixture was stirred at room temperature for 1 hour and left to stand overnight. The mixture was evaporated to dryness and the residue was dissolved in ethyl acetate and washed with sodium hydroxide solution (2M) and water, dried (anhydrous magnesium sulphate) and filtered. The filtrate was evaporated to dryness to give methyl 4-chloro-2-(N-methyl-N-methylsulphonylamino)benzoate (4.9 g) as a white solid, m.p. 73–75° C.

By proceeding in a similar manner the following compounds were prepared from the appropriately substituted starting materials:

methyl 2-chloro-4-(N-methyl-N-methylsulphonylamino) benzoate, NMR (DMSO-$d_6$) 3.05(s,3H) 3.35(s,3H) 3.85 (s,3H) 7.5(d,1H) 7.6(s,1H) 7.85(d,1H);

methyl 2-(N-methyl-N-methylsulphonylamino)-4-nitrobenzoate, NMR (DMSO-$d_6$) 3.05(s,3H) 3.25(s,3H) 3.8(s,3H) 8.0(d,1H) 8.3(d,1H) 8.4(s,1H);

ethyl 4-chloro-2-(N-ethyl-N-methylsulphonylamino) benzoate, NMR (CDCl$_3$) 1.1(t,3H) 1.35(t,3H) 2.9(s,3H) 3.65(q,2H) 4.3(q,2H) 7.3(d,1H) 7.35(s,1H) 7.8(d,1H);

methyl 3,4-dichloro-2-(N-methyl-N-methylsulphonyl) aminobenzoate, NMR (CDCl$_3$); 2.95(s,3H), 3.28(s,3H), 3.89(s,3H), 7.5(d,1H), 7.71(d,1H);

methyl 2-(N-methyl-N-methylsulphonyl)amino-4-trifluoromethoxybenzoate, NMR (CDCl$_3$) 2.95(s,3H), 3.3 (s,3H), 3.95(s,3H), 7.25(m,2H), 8.0(d,1H);

methyl 5-chloro-2-(N-methyl-N-methylsulphonyl) aminobenzoate, m.p. 91–93° C.;

methyl 4-chloro-2-(N-isobutyl-N-methylsulphonyl) aminobenzoate, m.p. 89–90° C., employing isobutyl iodide instead of methyl iodide;

methyl 4-chloro-2-(N-methyl-N-propylsulphonyl) aminobenzoate as an orange oil;

methyl 2-(N-methyl-N-methylsulphonyl)-aminobenzoate, m.p. 60–62° C.

Reference Example 7

Methyl iodide (22.0 ml) was added to a stirred suspension of 4-methyl-2-(N-methylsulphonylamino)benzoic acid (8.0 g) and anhydrous potassium carbonate (24.2 g) in acetone and the mixture was stirred and heated at reflux overnight. The mixture was cooled and filtered and the filtrate was evaporated to dryness. The residue was dissolved in dichloromethane and washed with aqueous sodium bicarbonate solution, water, dried (magnesium sulphate) and filtered. The filtrate was evaporated to dryness to give methyl 4-methyl-2-(N-methyl-N-methylsulphonylamino)benzoate (8.36 g) as a cream solid, m.p. 100–103° C.

By proceeding in a similar manner the following compounds were prepared from the appropriately substituted starting materials:

methyl 4-(N-methyl-N-methylsulphonylamino)-2-nitrobenzoate, NMR ($CDCl_3$) 2.95(s,3H) 3.4(s,3H) 3.9(s,3H) 7.7(d,1H) 7.75(d,1H) 7.85(s,1H);

propyl 4-chloro-2-(N-methylsulphonyl-N-propylamino)benzoate m.p. 81–83° C.;

ethyl 2-(N-ethyl-N-methylsulphonylamino)-4-methylsulphonylbenzoate m.p. 108.6–109.4° C.;

methyl 2-(N-methyl-N-methylsulphonyl)amino-4-trifluoromethylbenzoate, NMR ($CDCl_3$) 2.93(s,3H), 3.3 (s,3H), 3.9(s,3H), 7.65(m,2H), 8.0(dd, 1H);

methyl 4-bromo-2-(N-methyl-N-methylsulphonyl)aminobenzoate, NMR ($CDCl_3$) 2.95(s,3H), 3.23(s,3H), 3.83(s,3H), 7.5(dd,1H), 7.58(d,1H), 7.75(d,1H);

methyl 4-chloro-2-(N-ethylsulphonyl-N-methyl)aminobenzoate;

methyl 2-bromo-4-(N-methyl-N-methylsulphonyl)aminobenzoate, NMR ($CDCl_3$); 2.9(s,3H), 3.38(s,3H), 3.93(s,3H), 7.46(dd,1H), 7.68(d,1H), 7.87(d,1H);

methyl 2,4-bis(N-methyl-N-methylsulphonyl)aminobenzoate NMR ($CDCl_3$); 2.9(s,3H), 2.96(s,3H), 3.23(s,3H), 3.79(s,3H), 3.87(s,3H), 7.42(dd,1H), 7.48(d, 1H), 7.95(d,1H);

methyl 4-fluoro-2-(N-methyl-N-methylsulphonyl)aminobenzoate NMR ($CDCl_3$); 2.97(s,3H), 3.23(s,3H), 3.87(s,3H), 7.06–7.24(m,2H), 7.96(m,1H);

methyl 2-(N-methyl-N-methylsulphonyl)amino-4-methylsulphonylbenzoate NMR (acetone-d6); 3.02 (s,3H), 3.22(s,3H), 3.35(s,3H), 3.9(s,3H), 8.06(m,2H), 8.17(m,1H);

methyl 2-fluoro-4(N-methyl-N-methylsulphonyl)aminobenzoate as an orange oil, NMR ($CDCl_3$) 2.89(s, 3H), 3.34(s,3H), 3.91(s,3H), 7.1(m,2H), 7.93(t,1H);

methyl 3,4-difluoro-2-(N-methyl-N-methylsulphonyl)aminobenzoate as an orange solid, NMR ($CDCl_3$) 3.01(s, 3H), 3.3(s,3H), 3.91(s,3H), 7.24(q,1H), 7.73(m,1H);

methyl 4-chloro-2-(N-methyl-N-phenylsulphonyl)aminobenzoate as a white solid, m.p. 100–107° C.;

methyl 4-chloro-2-(N-methyl-N-benzylsulphonyl-N-methyl)aminobenzoate as a cream solid, m.p. 89–91° C.

Reference Example 8

A solution of methanesulphonyl chloride (6.3 g) in dichloromethane was added to a stirred, cooled (0–5° C.) solution of methyl 2-amino-4-chlorobenzoate (9.5 g) in dichloromethane. Triethylamine (7.1 g) was then added and the mixture was stirred at 0–5° C. for 10 minutes and then at room temperature for 0.5 hours.

The mixture was diluted with 2N hydrochloric acid. The organic phase was separated, washed with water, dried and evaporated. The crude product was purified by column chromatography to yield methyl 4-chloro-2-(N-methylsulphonylamino)benzoate as a white solid, (3.6 g) m.p. 125.5–128.1° C.

By proceeding in a similar manner the following compounds were prepared from the appropriately substituted starting materials:

methyl 2-(N-methyl-N-methylsulphonyl)amino-4-(N,N-bis-methylsulphonylamino)benzoate as an orange gum, NMR ($CDCl_3$) 2.57(s,3H), 3.2(s,3H), 3.4(s,6H), 3.94(s,3H), 7.4 (m,1H), 7.5(m,1H), 7.97(d,1H);

methyl 2-(N-methylsulphonylamino)benzoate, m.p. 88–90° C.

Reference Example 9

Concentrated sulphuric acid (20 ml) was added to a suspension of 2-chloro-4-(N-metbylsulphonylamino)benzoic acid (10.3 g) in methanol and the mixture was stirred and heated at reflux for 22 hours. It was cooled, evaporated to dryness and diluted with water, extracted with ethyl acetate, washed with aqueous sodium bicarbonate solution, water, dried (magnesium sulphate) and filtered. The filtrate was evaporated to dryness to give methyl 2-chloro-4-(N-methylsulphonylamino)benzoate(10.0 g) as an off-white solid, NMR (DMSO-$d_6$) 3.15(s,3H) 3.85(s,3H) 7.2(d,1H) 7.3(s,1H) 7.85(d,1H) 10.5(s,1H).

By proceeding in a similar manner the following compounds were prepared from the appropriately substituted starting materials:

methyl 2-(N-methylsulphonylamino)-4-nitrobenzoate, NMR ($CDCl_3$): 3.15 (s,3H) 4.0(s,3H) 7.9(d,1H) 8.25(d, 1H) 8.5(s,1H) 10.65(s,1H);

methyl 3,4-dichloro-2-(N-methyl-N-methylsulphonyl)aminobenzoate, NMR ($CDCl_3$); 2.95(s,3H), 3.28(s,3H), 3.89(s,3H), 7.5(d,1H), 7.71(d,1 H);

methyl 2-chloro4-(N-methyl-N-methylsulphonyl)aminobenzoate, NMR (DMSO $d_6$) 3.0(s,3H), 3.35(s,3H), 3.82(s,3H), 7.5(dd, 1H), 7.63(d,1H), 7.87(d,1H).

methyl 2-amino-4-trifluoromethylbenzoate m.p. 60–62° C.;
methyl 2-amino-4-methylbenzoate m.p. 41–43° C.;
methyl 4-bromo-2-nitrobenzoate m.p. 41–43° C.;
methyl 2-bromo-4-nitrobenzoate m.p. 83–85° C.;
methyl 2-amino-3,4-dichlorobenzoate, NMR ($CDCl_3$); 3.9 (s,3H), 6.4(bs,2H), 6.7–7.7(m,2H);
methyl 2-amino-3,4-difluorobenzoate.

Reference Example 10

A mixture of 2-chloro-4-(N-methylsulphonylamino)benzoic acid and 2-chloro-4-[N,N-bis(methylsulphonyl)amino]benzoic acid (3.6 g) in aqueous sodium hydroxide (2M) and methanol was stirred and heated at reflux for 0.5 hours. It was cooled and the methanol was removed by evaporation. The aqueous residue was acidified and the product was filtered off to give 2-chloro-4-(N-methylsulphonylamino)benzoic acid (3.4 g) as a white solid, m.p. 256–258° C.

By proceeding in a similar manner the following compounds were prepared from the appropriately substituted starting materials:

2-(N-methylsulphonylamino)-4-nitrobenzoic acid, NMR (DMSO-$d_6$) 3.3(s,3H) 7.9(d,1H) 8.2(d,1H) 8.35(s,1H) 10.5–11.1(bs,1H);

N-(methylsulphonyl)aniline, starting from [N,N-(bis)methylsulphonyl]aniline.

Reference Example 11

An aqueous solution of sodium hydroxide (11.0 g) was added to a solution of a mixture of methyl 4-methyl-2-(N,N-bis(methylsulphonyl)amino]benzoate and methyl 4-methyl-2-(N-methylsulphonylamino)benzoate (23.26 g) in methanol and the resulting suspension was heated at reflux for 1 hour. It was cooled and the methanol was removed by evaporation. The aqueous solution was acidified and the resultant solid was filtered off to give 4-methyl-2-(N-methylsulphonylamino)benzoic acid (16.42 g) as a cream solid, m.p. 202–205° C.

By proceeding in a similar manner the following compounds were prepared from the appropriately substituted starting materials:

4-(N-methylsulphonylamino)-2-nitrobenzoic acid, NMR (DMSO-d$_6$) 3.2(s,3H) 7.5(d,1H) 7.6(s,1H) 7.9(d,1H) 10.8 (s,1H) 13.3–14.1(bs,1H);

4-bromo-2-(N-methylsulphonyl)aminobenzoic acid m.p. 178–186° C.;

4-chloro-2-(N-ethylsulphonyl)aminobenzoic acid m.p. 177–179° C.;

2-bromo-4-(N-methylsulphonyl)aminobenzoic acid m.p.244–245° C.;

4-fluoro-2-(N-methylsulphonyl)aminobenzoic acid NMR (DMSO-d$_6$) 3.33(s,3H), 7.0(m,1H), 7.36(dd,1H), 8.08(m, 1H), 10.92(brs,0.5H);

2-chloro-4-(N-methylsulphonyl)aminobenzoic acid NMR (DMSO-d$_6$) 3.1(s,3H), 7.24(dd,1H), 7.29(d,1H), 7.85(d, 1H), 10.38(brs,1H), 13.08(bs,1H).

Reference Example 12

Methanesulphonyl chloride (5.72 g) was added to a stirred, cooled (0° C.) mixture of 4-amino-2-chlorobenzoic acid (6.9 g) and triethylamine (13.1 g) in acetonitrile. The mixture was then stirred at room temperature for 3.5 hours. Triethylamine (4 g) was added and the mixture was cooled to 0° C. and further methanesulphonyl chloride (3.8 g) was added. The mixture was then stirred at room temperature for one hour. The mixture was filtered and the filtrate evaporated. The residue was dissolved in 2N sodium hydroxide solution and washed with diethyl ether. The aqueous solution was acidified to pH 2–3 with 2N hydrochloric acid and then extracted with ethyl acetate. The organic extracts were evaporated. The residue was triturated with diethyl ether to yield a mixture of 2-chloro-4-(N-methylsulphonylamino) benzoic acid and 2-chloro-4-[N,N-bis(methylsulphonyl) amino]benzoic acid.

Reference Example 13

Methanesulphonyl chloride (12.2 ml) was added to a stirred, cooled solution of methyl 2-amino-4-methylbenzoate (10.3 g) and triethylamine (19.5 ml) in dichloromethane while maintaining the temperature below 0° C. The mixture was stirred at room temperature for 4 hours. Hydrochloric acid (2M) was added and the layers were separated. The organic layer was washed with water, dried (magnesium sulphate) and filtered. The filtrate was evaporated to dryness to give a mixture of methyl 4-methyl-2-[N,N-bis(methylsulphonyl)amino]benzoate and methyl 4-methyl-2-(N-methylsulphonylamino)benzoate (18.26 g) as a yellow solid which was not further purified.

By proceeding in a similar manner the following compounds were prepared from the appropriately substituted starting materials:

4-[N,N-bis-(methylsulphonyl)amino]-2-nitrobenzoic acid;

methyl 2-[N,N-bis(methylsulphonyl)amino]-4-methylsulphonylbenzoate;

N,N-bis(methylsulphonyl)aniline, m.p. 172–177.6° C.;

methyl 2-[N,N-bis(methylsulphonyl)]amino-4-trifluoromethylbenzoate m.p. 159–163° C.;

methyl 4-bromo-2-[N,N-bis(methylsulphonyl)] aminobenzoate, m.p. 221–225° C.;

methyl 4-chloro-2-(N-ethylsulphonyl)aminobenzoate and methyl 4-chloro-2-[N,N-bis(ethylsulphonyl)amino] benzoate;

methyl 2-bromo-4-[N,N-bis(methylsulphonyl)amino] benzoate and methyl 2-bromo-4-(N-methylsulphonyl)aminobenzoate;

methyl 2-(N-methyl-N-methylsulphonyl)amino-4-[N,N-bis (methylsulphonyl)amino]benzoate, NMR(CDCl$_3$), 2.97 (s,3H), 3.32(s,3H), 3.38(s,6H), 3.92(s,3H), 7.43(dd,1H), 7.52(d,1H), 7.98(d,1H);

methyl 4-fluoro-2-[N,N-bis(methylsulphonyl)amino] benzoate NMR (CDCl$_3$); 3.5(s,6H), 3.95(s,3H), 7.16(dd, 1H) 7.27(m,1H), 8.06(m,1H);

methyl 2-chloro-4-[N,N-bis(methylsulphonyl)amino] benzoate NMR (CDCl$_3$): 3.43(s,6H), 3.92(s,3H), 7.33(dd, 1H), 7.47(d,1H), 7.9(d,1H);

methyl 2-[N,N-bis(methylsulphonyl)amino]-4-methylsulphonyl benzoate m.p. 207.4–211.2° C.;

methyl-2-(N,N-bis(methylsulphonyl)amino]-4-nitrobenzoate as a yellow solid, NMR (CDCl$_3$) 3.5(s,6H), 4.0(s,3H), 8.18(d,1H), 8.26(m,1H), 8.39(m,1H);

methyl 2-fluoro4-[N,N-bis(methylsulphonyl)amino] benzoate as a white solid. NMR (CDCl$_3$) 3.42(s,6H), 3.95(s,3H), 7.21(m,2H), 8.04(t,1H);

methyl 3.4-difluoro-2-[N,N-bis(methylsulphonyl)amino] benzoate as a solid, NMR (CDCl$_3$) 3.42(s,6H), 3.87(s, 3H), 7.3(q,1H) 7.79(m,1H);

methyl 2-[N,N-bis(methylsulphonyl)amino]-4-trifluoromethylbenzoate as an orange oil;

methyl 2-(N-methylsulphonyl)amino-4-trifluoromethoxybenzoate and methyl 2-[N,N -bis (methylsulphonyl)amino]-4-trifluoromethoxybenzoate;

methyl 5-chloro-2-(N-methylsulphonyl)aminobenzoate and methyl 5-chloro-2-[N,N-bis(methylsulphonyl)amino] benzoate, m.p. 136–138° C.;

methyl 4-chloro-2-[N,N-bis(propylsulphonyl)amino] benzoate as a brown oil;

methyl 4-chloro-2-[N,N-bis-(phenylsulphonyl)amino] benzoate as a cream solid, m.p. 156.5–158° C.;

methyl 2-[N,N-bis-(benzylsulphonyl)amino]-4-chlorobenzoate as a brown solid.

Reference Example 14

A mixture of ethyl 2-(N-ethyl-N-methylsulphonylamino)-4-methylsulphonylbenzoate (11.4 g) and lithium hydroxide monohydrate (1.37 g) in aqueous ethanol (50%) was stirred at room temperature for 19 hours. The mixture was then acidified with conc. hydrochloric acid and extracted with ethyl acetate. The combined organic extracts were dried (magnesium sulphate), filtered and evaporated to yield 2-(N-ethyl-N-methylsulphonylamino)-4-methylsulphonylbenzoic acid as a brown solid (9.48 g), NMR (acetone-d$_6$); 1.15(t, 3H), 2.98(s,3H), 3.22(s.3H), 3.85(q,2H), 8.0–8.25(m,3H).

By proceeding in a similar manner 2-(N-methyl-N-methylsulphonyl)amino-4-methylsulphonylbenzoic acid was prepared, m.p. 199–200° C.

Reference Example 15

A suspension of methyl 2-[N,N-bis(methylsulphonyl) amino]-4-methylsulphonylbenzoate (22.9 g) and lithium hydroxide monohydrate (7.5 g) in aqueous methanol (50%) was stirred at room temperature for 18 hours. The resulting solution was acidified with concentrated hydrochloric acid and extracted with ethyl acetate. The combined organic extracts were dried (magnesium sulphate), filtered and evaporated to yield 2-methylsulphonylamino-4-methylsulphonylbenzoic acid as a beige solid. NMR (acetone d$_6$): 3.1(2s,6H). 7.57(dd,1H), 8.15(d,1H), 8.23(d, 1H).

By proceeding in a similar manner the following compounds were prepared from the appropriately substituted starting materials:

2-(N-methylsulphonyl)amino-4-trifluoromethylbenzoic acid as an orange oil;
2-(N-methyl-N-methylsulphonyl)amino-4-(N-methylsulphonylamino)benzoic acid as an orange solid;
2-(N-methylsulphonyl)amino-4-methylsulphonylbenzoic acid.

The following compounds were prepared using sodium hydroxide in place of lithium hydroxide:
2-(N-methylsulphonyl)amino-4-nitrobenzoic acid as an orange solid;
2-fluoro-4-(N-methylsulphonyl)aminobenzoic acid as a brown solid, NMR (DMSO) 3.26(s,3H), 7.04(m,2H), 7.85(t,1H), 10.5(s,1H), 13.0(s,1H);
3,4-difluoro-2-(N-methylsulphonyl)aminobenzoic acid as a brown solid;
4-chloro-2-(N-propylsulphonyl)aminobenzoic acid, m.p. 159–160° C.;
4-chloro-2-(N-phenylsulphonyl)aminobenzoic acid, m,.p. 186.5–189° C.;
4-chloro-2-(N-benzylsulphonyl)aminobenzoic acid, m p. 181–185° C.

Reference Example 16

Concentrated hydrochloric acid (90 ml) was added to a stirred suspension of methyl 2-nitro-4-methylsulphonyl benzoate (25 g) in methanol at −5° C. (ice/salt bath). The cooling bath was then removed and iron dust (17.5 g) was added portionwise over a period of 20 minutes. The resulting exotherm was controlled using a cooling bath so that the temperature did not exceed 50° C. After 15 minutes of cooling, the bath was removed and the reaction mixture was allowed to reach room temperature. Stirring was continued for a further 3 hours. The mixture was poured onto ice and then neutralised with sodium carbonate. Dichloromethane was added and the suspension was filtered. The filtrate was extracted with further dichloromethane and the combined organic extracts were dried (magnesium sulphate), filtered and evaporated to yield a crude product which was purified by recrystallisation from ethyl acetate/hexane to give methyl 2-amino-4-methylsulphonyl benzoate (4.5 g) as yellow needles, m.p. 98.3–98.5° C.

By proceeding in a similar manner, the following compounds were prepared from the appropriately substituted starting material:
methyl 2-amino-4-bromobenzoate NMR (CDCl$_3$) 3.8(s,3H), 5.72(bs,2H), 6.7(dd,1H), 6.79(d,1H), 7.65(d,1H);
methyl 4-amino-2-bromobenzoate m.p. 93–95° C.

Reference Example 17

A mixture of methyl 2-amino-3,4-dichlorobenzoate (2.2 g) and methanesulphonyl chloride (2.86 g) was stirred at 100° C. for 4 hours. A further quantity of methanesulphonyl chloride (2.86 g) was added and the mixture was stirred at 100° C. overnight. The mixture was poured into water then extracted with ethyl acetate. The combined organic extracts were washed with water, dried (magnesium sulphate) and evaporated to yield a brown oil which was crystallised from cyclohexane/ethyl acetate to yield methyl 3,4-dichloro-2-(methylsulphonylamino)benzoate as light brown crystals (1.4 g), m.p. 100–102° C.

Reference Example 18

A solution of N-(methylsulphonyl)aniline (4.55 g) in dimethoxyethane was added under an inert atmosphere to a stirred suspension of sodium hydride (80% oil dispersion, 0.8 g) in dimethoxyethane at room temperature. The resulting white emulsion was stirred at 37° C. for 30 minutes. Diphenyliodonium-2-carboxylate monohydrate (10 g) and cupric acetate (0.3 g) were then added and the suspension was stirred at reflux for 24 hours. The mixture was cooled to room temperature and water was added. The mixture was made alkaline by addition of 2M NaOH solution then filtered through 'HYFLO' silica. The filtrate was acidified with concentrated hydrochloric acid and then extracted with ethyl acetate. The combined organic extracts were dried (magnesium sulphate) and evaporated to yield 2-(N-methylsulphonyl-N-phenyl)aminobenzoic acid.

Reference Example 19

A suspension of 4-bromo-2-nitrotoluene (50 g) in water was heated to 97° C. Potassium permanganate (240 g) was then added over a period of 4.5 hours. The resulting suspension was heated at reflux overnight. The mixture was filtered whilst hot (through 'HYFLO' silica). The filter cake was washed through with boiling water. The cooled filtrates were washed with diethyl ether then acidified to pH 1 with concentrated hydrochloric acid. The resulting suspension was cooled in ice water and then filtered. The solid was dried to yield 4-bromo-2-nitrobenzoic acid (10.83 g) as a cream solid, m.p. 164–167° C.

Reference Example 20

A suspension of methyl 2-(N-methyl-N-methylsulphonylamino)-4-nitrobenzoate (2.88 g), iron powder (5 g) and calcium chloride (0.5 g) in ethanol was stirred at reflux for 2 hours. The suspension was filtered whilst hot. The filter cake was thoroughly washed with boiling ethanol. The, combined filtrates were cooled to room temperature then evaporated to dryness to yield methyl 4-amino-2-(N-methyl-N-methylsulphonyl)-aminobenzoate (3 g) as a light brown solid, NMR (CDCl$_3$); 3.0(s,3H), 3.21(s,3H), 3.8(s, 3H), 3.6–4.15(bs,2H), 6.6(dd,1H), 6.7(d,1H), 7.83(d,1H).

Reference Example 21

Sodium hydride (60% oil dispersion, 1.0 g) was stirred in dry toluene under an inert atmosphere and methanesulphonamide (0.8 g) was added. After heating at reflux for 1 hour and cooling, 2-bromo-3-chloro4-trifluoromethoxybenzoic acid (2.69 g) was added. After the effervescence had subsided, copper (I) bromide (0.72 g) was added and the mixture heated at reflux for 8 hours. Two further additions of copper (I) bromide (total 1.42 g) were made, with reflux maintained for a further 12 hours. After cooling, a solution of potassium bisulphate was added and the mixture extracted (ethyl acetate), dried (magnesium sulphate) and evaporated to dryness to give 3-chloro-2-(N-methylsulphonyl)amino-4-trifluoromethoxybenzoic acid as a white solid (4.14 g). This was used without further purification in the next stage according the following procedure.

This product (1.7 g) was heated at reflux for 10 hours with stirring with methyl iodide (3.68 ml) and anhydrous potassium carbonate (4.14 g) in acetone. Additional methyl iodide (26 ml) was added with heating at reflux for 12 hours. The solvent was evaporated in vacuo and the residue partitioned between water and dichloromethane. The organic layer was dried (magnesium sulphate) and evaporated to give methyl 3-chloro-2-(N-methyl-N-methylsulphonyl)4-trifluoromethoxybenzoate (1.73 g) as an oil, NMR (CDCl$_3$) 2.95(s,3H), 3.25(s,3H), 3.90(s,3H), 7.35(m,1H), 7.80(d,1H).

Reference Example 22

A solution of 3-chloro-4-trifluoromethoxybenzoic acid (4.15 g) in dry tetrahydrofuran was treated with n-butyl lithium (15.1 ml of 2.5M solution in hexanes) at −78° C. under an inert atmosphere. After stirring overnight at this temperature, a solution of 1,2-dibromotetrachloroethane (839 g) in tetrahydrofuran was added. After 30 minutes, the solution was allowed to slowly warm to ambient temperature, then treated with 2M hydrochloric acid. The mixture was extracted with ether, the ethereal solution itself extracted with sodium bicarbonate solution and the latter acidified with dilute hydrochloric acid. This solution was extracted with ether and evaporated in vacuo to give 2-bromo-3-chloro-4-trifluoromethoxybenzoic acid (5.5 g) as a brown solid, NMR (CDCl$_3$) 7.3(m,1H), 7.8(d,1H).

Reference Example 23

A solution of n-butyl lithium (4.4 ml of 2.5M solution in hexanes) in dry diisopropyl ether was treated at −78° C. under an inert atmosphere with 3-chloro4-trifluoromethoxy-bromobenzene (2.96 g) in diisopropyl ether. After 10 minutes, excess carbon dioxide (in the form of pellets) was added and the mixture left to slowly warm to ambient temperature. Ice-water was added and the organic layer run off. The aqueous layer was acidified with dilute hydrochloric acid, extracted (ether), dried (magnesium sulphate) and evaporated to dryness to give 3-chloro-4-trifluoromethoxybenzoic acid (1.51 g) as a white solid, m.p. 110.5–111.5° C.

Reference Example 24

A solution of 3-chloro4-trifluoromethoxyaniline (5.1 g) in acetic acid (31 ml) was stirred and treated with sodium nitrite (2.16 g) in concentrated sulphuric acid (14 ml) at below 18° C. After an additional 1 hour at 10° C., the solution was added to a mixture of copper (I) bromide (7.7 g) and hydrobromic acid (24.5 ml) in water at 40–50° C. The reaction was completed by heating at 50° C. for 2 hours, water was added and the mixture filtered. The filtrate was extracted with ether, washed with sodium bicarbonate, dried (magnesium sulphate) and evaporated to give 3-chloro-4-trifluoromethoxy-bromobenzene (6.05 g) as a brown oil, NMR (CDCl$_3$) 7.10(m,1H), 7.35(m,1H), 7.55(d,1H).

By proceeding in a similar manner 2-nitro-4-trifluoromethoxy-bromobenzene was prepared, NMR (CDCl$_3$) 7.35(m,1H), 7.75(m,1H), 7.8(d,1H).

Reference Example 25

A solution of anhydrous tin (II) chloride (17.14 g) in concentrated hydrochloric acid was added to a solution of 3-chloro-4-trifluoromethoxy-nitrobenzene (5.2 g) in ethanol with cooling to maintain a temperature below 30° C. After an additional 2 hours at ambient temperature and 0.5 hour at 50° C., the mixture was poured onto water, basified with sodium hydroxide solution and extracted with ether. The extracts were washed with water, dried (magnesium sulphate) and evaporated in vacuo to give an oil (6.2 g), which was purified by chromatography eluting with dichloromethane to give 3-chloro4-trifluoromethoxyaniline (4.1 g), m.p. 32–33° C. as a yellow solid.

Reference Example 26

A stirred mixture of 2-trifluoromethoxy-5-nitroaniline (8.61 g) and concentrated hydrochloric acid in water was stirred at 0° C. and treated with sodium nitrite (2.93 g) in water (7 ml). After 1 hour at 0° C. the solution was added to a stirred solution of copper (I) chloride (4.4 g) in water and concentrated hydrochloric acid keeping below 20° C. After stirring overnight the mixture was diluted with water, extracted with ether and the extracts dried (magnesium sulphate) and evaporated to give an oil (8.7 g). This was purified by chromatography eluting with hexane/ethyl acetate (98:2) to give 3-chloro-4-trifluoromethoxy-nitrobenzene (5.2 g) as a yellow liquid, NMR (CDCl$_3$) 7.50(m,1H), 8.20(m,1H), 8.4(d,1H).

Reference Example 27

A mixture of potassium hydroxide (4.71 g) and 5-nitro-2-trifluoromethoxyacetanilide (20 g) in ethanol and water was heated at reflux for 3.5 hours, poured onto ice and the resulting solid filtered off and dried. Purification by chromatography, eluting with hexane/ethyl acetate gave 2-trifluoromethoxy-5-nitroaniline (9.8 g) as a yellow solid, m.p. 90–91° C.

Reference Example 28

2-Trifluoromethoxyacetanilide (31.6 g) was added to stirred concentrated sulphuric acid at −10° C. A mixture of concentrated nitric acid and concentrated sulphuric acid was added maintaining at −5° C. to −10° C. The mixture was stirred at 0° C. for four hours and poured onto excess ice. The filtered solid was dissolved in dichloromethane, washed with water, dried (magnesium sulphate) and evaporated to yield a residue. This was purified by chromatography eluting with hexane/ethyl acetate to give 5-nitro-2-trifluoromethoxyacetanilide (21.57 g), m.p. 129–130° C.

Reference Example 29

Acetyl chloride (66 ml) was added to a stirred solution of 2-trifluoromethoxyaniline (150 g) and triethylamine in dry dichloromethane (maintaining a temperature below 20° C.). After 3 hours additional stirring at 20° C. the mixture was washed with dilute hydrochloric acid, sodium carbonate solution and water, dried (magnesium sulphate) and evaporated to dryness. The residue was recrystallised from toluene to furnish 2-trifluoromethoxyacetanilide (113.4 g), m.p. 64–66.5° C.

Reference Example 30

6,7-Difluoroisatin (22.2 g) was added to a solution of sodium hydroxide (2N, 185 ml). Hydrogen peroxide (30%, 36 ml) was added at 40° C. or less over 20 minutes. After 1 hour the mixture was heated to 65° C. for 0.5 hours, cooled, poured onto water and acidified with concentrated hydrochloric acid. The resulting solid was filtered, washed with water and recrystallised from ethyl acetate/cyclohexane to give 2-amino-3,4-difluorobenzoic acid (11.3 g) as an orange solid, m.p. 207–208° C.

Reference Example 31

2,3-Difluoro-α-isonitrosoacetanilide (36.8 g) was added during 1 hour to a stirred solution of concentrated sulphuric acid and water at 65–75° C. After an additional 20 minutes at 80° C., the cooled mixture was poured onto excess ice-water. Extraction with ethyl acetate was followed by water washing, drying (magnesium sulphate) and evaporation to dryness to give a brown solid. Trituration with boiling cyclohexane gave after cooling, 6,7-difluoroisatin (22.2 g), m.p. 164.5–167° C. as a brown solid.

Reference Example 32

Chloral hydrate (38.9 g) was added to a stirred solution of sodium sulphate (219 g) in water. A solution of 2,3- difluoroaniline (25 g) in a mixture of concentrated hydrochloric acid (19.4 ml) and water (117 ml) was added. A solution of hydroxylamine hydrochloride (41.35 g) in water was then added over 35 minutes and the mixture stirred for 1 hour at 95–100° C. After cooling the solid was filtered, washed with water, then with petroleum ether and dried in a desiccator to furnish 2,3-difluoro-α-isonitrosoacetanilide (36.8 g), m.p. 124.5–125° C.

Reference Example 33

A solution of sodium hydroxide (2.38 g) in water was added to a mixture of methyl 2-(N-methylsulphonyl)amino-4-trifluoromethoxybenzoate and methyl 2-[N,N-bis(methylsulphonyl)amino]-4-trifluoromethoxybenzoate (8.26 g) in methanol at 15–20° C. After an additional 15 minutes the solid was filtered, dissolved in ethyl acetate, dried (magnesium sulphate) and evaporated in vacuo to give methyl 2-(N-methylsulphonyl)amino-4-trifluoromethoxybenzoate as a brown solid (4.15 g) after trituration with hexane, NMR (CDCl$_3$) 3.0(s,3H), 3.9(s,3H), 6.9(m,1H), 7.55(m,1H), 8.05(d,1H), 10.5(brs, 1H).

By proceeding in a similar manner methyl 5-chloro-2-(N-methylsulphonyl)aminobenzoate was prepared m.p. 117–120° C.

Reference Example 34

Methyl 2-nitro-4-trifluoromethoxybenzoate (10 g) and 5% palladium on activated carbon (0.5 g) in methanol was hydrogenated for 20 hours at ambient temperature. The mixture was filtered and the filtrate evaporated to give methyl 2-amino-4-trifluoromethoxybenzoate (8.35 g) as a brown oil, NMR (CDCl$_3$) 3.9(s,3H), 5.9(brs,2H), 6.55(m, 2H), 7.9(d,1H).

Reference Example 35

2-Nitro-4-trifluoromethoxybenzoic acid (4.7 g) was heated under reflux conditions for 2 hours with oxalyl chloride (1.95 ml) and 1,2-dichloroethane (25 ml) containing N,N-dimethylformamide (2 drops). The solvents were evaporated to dryness, the residue dissolved in drv dichloromethane and added to a solution of triethylamine (2.08 g) in dry methanol. After 2 days, the solvent was evaporated and the residue partitioned between dichloromethane and sodium bicarbonate solution. The organic phase was dried (magnesium sulphate), evaporated and the residue purified by chromatography, eluting with dichloromethane/hexane to give methyl 2-nitro-4-trifluoromethoxybenzoate (4.9 g) as a yellow liquid, NMR (CDCl$_3$) 3.9(s,3H), 7.5(m,1H), 7.75 (brs, 1H), 7.85(d,1H).

Reference Example 36

A mixture of 2-nitro-4-trifluoromethoxybenzonitrile (8.7 g) and a 55% sulphuric acid solution (46 ml) was heated under reflux conditions for 2 hours, the mixture poured onto ice and extracted with ether. The ether extracts were washed with water and back-extracted with sodium hydroxide solution. Re-acidification of this aqueous extract and subsequent extraction with ether gave a solution which was dried (magnesium sulphate) and evaporated to yield 2-nitro-4-trifluoromethoxybenzoic acid (8.5 g) as a cream solid, NMR (d$_6$ DMSO) 3.3(brs,1H), 7.8(m,1H), 8.05(d,1H), 8.15(m, 1H).

Reference Example 37

A solution of 2-nitro-4-trifluoromethoxy-bromobenzene (2.0 g) in N,N-dimetbylformamide (2 ml) was treated with copper (I) cyanide (0.62 g) and the mixture heated at 150° C. for 1 hour. Toluene (10 ml) was added and the mixture was maintained at reflux for 1 hour. The mixture was filtered and the filtrate evaporated to give a dark oil which was purified by chromatography eluting with ethyl acetate/hexane (1:9) to give 2-nitro-4-trifluoromethoxybenzonitrile (1.1 g) as a yellow liquid, NMR (CDCl$_3$) 7.65(m,1H), 8.0(d,1H), 8.15(m,1H).

Reference Example 38

Sodium hydride (4.6 g) in dry dioxan was stirred whilst adding N-methylmethanesulphonamide (6.4 g). When the effervescence had subsided, 2-chloro-4,5-difluorobenzoic acid (10.0 g) was added portionwise, followed by copper (I) chloride (1.7 g) and the mixture heated under reflux conditions overnight. After evaporation to dryness, hydrochloric acid (2N, 100 ml) was added and the mixture extracted with dichloromethane. The extract was dried (magnesium sulphate) and evaporated to dryness. The residue was dissolved in acetone, filtered and the filtrate evaporated and triturated with ether to give 4,5-difluoro-2-(N-methyl-N-methylsulphonyl)aminobenzoic acid, m.p.159–160.5° C.

By proceeding in a similar manner the following compounds were prepared:
4-iodo-2-(N-methyl-N-methylsulphonyl)aminobenzoic acid, m.p. 174–175° C. from 2-chloro-4-iodobenzoic acid;
4-chloro-2-(N-methylsulphonylamino)benzoic acid, m.p. 188–192° C. from 2-bromo-4-chlorobenzoic acid, employing copper (I) bromide and methanesulphonamide and 3 equivalents of sodium hydride;
4-chloro-2-(N-methyl-N-isopropylsulphonyl)aminobenzoic acid, m.p. 178–180° C., from 2-bromo-4-chlorobenzoic acid with copper (I) bromide and N-methyl-isopropylsulphonarnide;
4-chloro-2-(N-methoxy-N-methylsulphonyl)aminobenzoic acid, m.p. 159–160° C. from 2-bromo-4-chlorobenzoic acid employing copper (I) bromide and N-methoxy-methanesulphonamide.

Reference Example 39

Thionyl chloride (21 ml) was added to methanol at 10° C. and the solution stirred for 0.5 hours before being added to 4-chloro-2-(methylsulphonylamino)benzoic acid (11.1 g). The mixture was heated under reflux conditions for 2 days after which time a further addition of thionyl chloride (6 ml) was made and reflux resumed for a further 2 days. The solvent was evaporated to dryness, water added and the mixture extracted with ethyl acetate. The extract was washed with sodium hydroxide solution (2N) then with water, dried (magnesium sulphate) and evaporated to dryness to give methyl 4-chloro-2-(methylsulphonylamino)benzoate (3.85 g) as a cream solid, NMR (CDCl$_3$) 3.25(s,3H), 3.9(s,3H), 7.3(dd,1H), 7.6(m,1H), 7.95(d,1H), 10.2(brs,1H).

Reference Example 40

A solution of the magnesium salt of t-butyl 3-cyclopropyl 3-oxopropanoate (1.85 g) in dry toluene was treated with a solution of 4-chloro-2-(N-methyl-N-phenylsulphonyl) aminobenzoyl chloride (3.19 g) in toluene (10 ml). After stirring overnight at ambient temperature, trifluoroacetic acid (1.6 ml) was added and the mixture stirred for 2 hours. The solution was washed (water), dried (magnesium sulphate), evaporated to dryness and the residue purified by chromatography eluting with dichloromethane. This gave 1-[4-chloro-2-(N-methyl-N-phenylsulphonyl)amino]

phenyl-3-cyclopropylpropan-1,3-dione (1.6 g) as an orange oil, NMR (CDCl$_3$) 1.0(m,2H), 1.25(m,2H), 2.15(m,1H), 3.1(s,3H), 5.25(s,2H), 6.4(dd,1H), 7.15–7.7(m,7H) (keto form).

By proceeding in a similar manner the following compounds were prepared:

1-[4-chloro-2-(N-benzylsulphonyl-N-methyl)amino] phenyl-3-cyclopropylpropan-1,3-dione as an orange gum, NMR (CDCl$_3$) 1.0(m,2H), 1.2(m,2H), 1.8(m,1H), 3.2(s, 3H), 4.4(s,2H), 4.4(s,2H), 6.15(s,1H), 6.85(dd,1H), 7.45 (m,7H), 16.0(brs,1H), enol form.

1[4-chloro-2-(N-methyl-N-isopropylsulphonyl)amino] phenyl-3-cyclopropylpropan-1,3-dione as an orange oil;

1-[4-chloro-2-(N-methoxy-N-methylsulphonyl)amino] phenyl-3-cyclopropylpropan-1,3-dione, m.p. 84–88° C.;

1-[4-chloro-2-(N-isobutyl-N-methylsulphonyl) aminophenyl]-3-cyclopropylpropan-1,3-dione, NMR (CDCl$_3$) 0.9(broad m,6H), 1.05(m,2H), 1.25(m,2H), 1.8 (m,1H), 2.1(broad m,1H), 3.05(s,3H), 3.38(broad m,2H), 6.1(s,1H), 7.32(m,2H), 16.1(brs,1H), enol form;

1-cyclopropyl-3-[3,4-difluoro-2-(N-methyl-N-methylsulphonyl)amino]phenylpropan-1,3-dione as an orange oil.

Reference Example 41

Magnesium (3.0 g) was stirred in methanol, carbon tetrachloride (0.5 ml) added and the mixture warmed at 50° C. until the metal had dissolved (1.5 hours). Tert-butyl 3-cyclopropyl-3-oxopropanoate (20.0 g) was then added dropwise and the mixture heated under reflux conditions for 1 hour. The solvent was evaporated and re-evaporated after addition of toluene to give tert-butyl 3-cyclopropyl-3-oxopropanoate magnesium salt (29.9 g) as a white solid, m.p. >300° C., IR max (C=O) 1520, 1540; (C—O) 1350 cm.

According to a feature of the present invention, there is provided a method for controlling the growth of weeds (i.e. undesired vegetation) at a locus which comprises applying to the locus a herbicidally effective amount of at least one isoxazole derivative of formula (I). For this purpose, the isoxazole derivatives are normally used in the form of herbicidal compositions (i.e. in association with compatible diluents or carriers and/or surface active agents suitable for use in herbicidal compositions), for example as hereinafter described.

The compounds of formula (I) show herbicidal activity against dicotyledonous (i.e. broad-leafed) and monocotyledonous (i.e. grass) weeds by pre- and/or post-emergence application. By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula (I) may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crus-galli, Sorghum bicolor, Elcusine indica* and Setaria spp, e.g. *Setaria faberii* or *Setaria viridis,* and sedges, for example, *Cyperus esculentus*. The amounts of compounds of formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non- directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose. When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required.

According to a further feature of the present invention, there are provided compositions suitable for herbicidal use comprising one or more of the isoxazole derivatives of formula (I), in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of formula (I), from 2 to 10% of surface-active agent, from 0.1 to 5% of thickener and from 15 to 87.9% of water;

wettable powders which comprise from 10 to 90% of one or more compounds of formula (I), from 2 to 10% of surface-active agent and from 8 to 88% of solid diluent or carrier;

water soluble or water dispersible powders which comprise from 10 to 90% of one or more compounds of formula (I), from 2 to 40% of sodium carbonate and from 0 to 88% of solid diluent;

liquid water soluble concentrates which comprise from 5 to 50%, e.g. 10 to 30%, of one or more compounds of formula (I), from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula (I), from 5 to 15% of surface-active agent, from 0.1 to 5% of thickener and from 10 to 84.9% of organic solvent;

granules which comprise from 1 to 90%, e.g. 2 to 10% of one or more compounds of formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine[2-chloro-4-ethylamino-6-isopropylamino-1,3,5-triazine], bromoxynil[3,5-dibromo-4-hydroxybenzonitrile], chlortoluron[N'-(3-chloro-4-methylphenyl)-N,N-dimethylurea], cyanazine[2-chloro-4-(1-cyano-1-methylethylamino)-6-ethylamino-1,3,5-triazine], 2,4-D[2,4-dichlorophenoxy-acetic acid], dicamba[3,6-dichloro-2methoxybenzoic acid], difenzoquat[1,2-dimethyl-3,5-diphenyl-pyrazolium salts], flampropmethyl[methyl N-2-(N-benzoyl-3-chloro-4-fluoroanilino)-propionate], fluometuron[N'-(3-trifluoro-methylphenyl)-N,N-dimethylurea], isoproturon [N'-(4isopropylphenyl)-N,N-dimethylurea], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chlorophenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the isoxazole derivatives of formula (I) or, as is preferred, a herbicidal composition as hereinbefore described, and preferably a herbicidal concentrate which must be diluted before use, comprising at least one of the isoxazole derivatives of formula (I) within a container for the aforesaid derivative or derivatives of formula (I), or a said herbicidal composition, and instructions physically associated with the aforesaid container setting out the manner in which the aforesaid derivative or derivatives of formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the isoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofuryl alcohol (THFA) | 10% v/v |
| Water | to 100 volumes. | by stirring THFA, active ingredient (compound 1) and 90% volume of water and slowly adding the potassium hydroxide soltuion until a steady pH 7–8 is obtained then making up to volume with water.

Similar soluble concentrates may be prepared as described above by replacing the isoxazole (compound 1) with other compounds of formula (I).

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compund 1) with other compounds of formula (I).

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of formula (I).

The compounds of the invention have been used in herbicidal applications according to the following procedures.

Method of Use of Herbicidal Compounds:

a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 litres of spray fluid per hectare.

b) Weed control: Pre-emergence

The seeds were sown in 70 mm square, 75 mm deep plastic pots in non-sterile soil. The quantities of seed per pot were as follows:

| | Approx number of seeds/pot |
|---|---|
| Weed species | |
| 1) Broad-leafed weeds | |
| Abutilon theoprasti | 10 |
| Amaranthus retroflexus | 20 |
| Galium aparine | 10 |
| Ipomoea purpurea | 10 |
| Sinapis arvensis | 15 |
| Xanthium strumarium | 2 |
| 2) Grass weeds | |
| Alopecurus myosuroides | 15 |
| Avena fatua | 10 |
| Echinochloa crus-galli | 15 |
| Setaria viridis | 20 |
| 3) Sedges | |
| Cyperus esculentus | 3 |
| Crop | |
| 1) Broad-leafed | |
| Cotton | 3 |
| Soya | 3 |
| 2) Grass | |
| Maize | 2 |
| Rice | 6 |
| Wheat | 6 |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| | | Number of plants per pot | Growth stage |
|---|---|---|---|
| 1) | Broad leafed weeds | | |
| | Weed species | | |
| | Abutilon theoprasti | 3 | 1–2 leaves |
| | Amaranthus retroflexus | 4 | 1–2 leaves |
| | Galium aparine | 3 | 1st whorl |
| | Ipomoea purpurea | 3 | 1–2 leaves |
| | Sinapis arvensis | 4 | 2 leaves |
| | Xanthium strumarium | 1 | 2–3 leaves |
| 2) | Grass weeds | | |
| | Weed species | | |
| | Alopecurus myosuroides | 8–12 | 1–2 leaves |
| | Avena fatua | 12–18 | 1–2 leaves |
| | Echinochloa crus-galli | 4 | 2–3 leaves |
| | Setaria viridis | 15–25 | 1–2 leaves. |
| 3) | Sedges | | |
| | Weed species | | |
| | Cyperus esculentus | 3 | 3 leaves. |
| 1) | Broad leafed | | |
| | Crops | | |
| | Cotton | 2 | 1 leaf |
| | Soya | 2 | 2 leaves. |
| 2) | Grass | | |
| | Crops | | |
| | Maize | 2 | 2–3 leaves |
| | Rice | 4 | 2–3 leaves |
| | Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the. percentage reduction in growth or damage to the crop or weeds, in comparison with the plants in the control pots.

The compounds of the invention, used at 4 kg/ha or less, have shown an excellent level of herbicidal activity together with crop tolerance on the weeds used in the foregoing experiments.

When applied pre- or post-emergence at 1000 g/ha compounds 1 to 34 gave at least 90% reduction in growth of one or more of the weed species.

What is claimed is:

1. A 4-benzoylisoxazole derivative of formula (I):

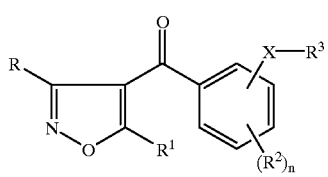

(I)

wherein:

R represents a hydrogen atom or a group —$CO_2R^4$;

$R^1$ represents:

a straight- or branched-chain alkyl group having up to six carbon atoms which is optionally substituted by one or more halogen atoms; or a cycloalkyl group having from three to six carbon atoms optionally substituted by one or more $R^5$ groups or one or more halogen atoms;

$R^2$ represents:

a halogen atom;

a straight- or branched-chain alkyl, alkenyl or alkynyl group having up to six carbon atoms optionally substituted by one or more halogen atoms;

a straight- or branched-chain alkyl group having up to six carbon atoms which is substituted by one or more $-OR^5$ groups;

a group selected from nitro, cyano, $-CO_2R^5$, $-S(O)_pR^6$, $-O(CH_2)_mOR^5$, $-COR^5$, $-NR^5R^6$, $-N(R^8)SO_qR^7$, $-CONR^9R^{10}$ and $-OR^{51}$;

phenyl optionally substituted by from one to three $R^{21}$ groups which are the same or different;

$R^3$ represents $-S(O)_qR^7$;

X represents a group $-N(R^8)-$;

n represents zero or an integer from one to four; where n is greater than one, the groups $R^2$ are the same or different;

$R^4$ represents a straight- or branched-chain alkyl group having up to six carbon atoms optionally substituted by one or more halogen atoms;

$R^5$, $R^{51}$ and $R^6$, which are the same or different, each represents:

a hydrogen atom;

a straight- or branched-chain alkyl, alkenyl or alkynyl group having up to six carbon atoms optionally substituted by one or more halogen atoms;

phenyl optionally substituted by from one to five $R^2$ groups which are the same or different; or a cycloalkyl group having from three to six carbon atoms;

$R^7$ represents:

a straight- or branched-chain alkyl, alkenyl or alkynyl group having up to six carbon atoms optionally substituted by one or more halogen atoms;

a cycloalkyl group having from three to six carbon atoms;

phenyl or benzyl optionally substituted by from one to five $R^{21}$ groups which are the same or different;

or $-NR^9R^{10}$;

$R^8$ represents:

a hydrogen atom; or a straight- or branched-chain alkyl, alkenyl or alkynyl group having up to ten carbon atoms optionally substituted by one or more halogen atoms;

a cycloalkyl group having from three to six carbon atoms;

phenyl optionally substituted by from one to five groups which are the same or different selected from halogen, nitro, cyano, $R^5$, $S(O)_pR^5$ and $-OR^5$; or a group $-OR^{11}$;

$R^9$ represents:

a hydrogen atom;

a straight- or branched-chain alkyl group having up to six carbon atoms optionally substituted by one or more halogen atoms;

or phenyl optionally substituted by from one to five $R^2$ groups which are the same or different;

$R^{10}$ represents a group selected from $R^5$ and $-OR^{11}$;

$R^{11}$ represents a straight- or branched-chain alkyl group having up to six carbon atoms;

$R^{21}$ represents:

a halogen atom;

a straight- or branched-chain alkyl group having up to three carbon atoms optionally substituted by one or more halogen atoms;

or a group selected from nitro, cyano, $-S(O)_pR^5$ and $-OR^5$;

m represents one, two or three;

p represents zero, one or two; and q represents zero or two;

or an agriculturally acceptable salt thereof.

2. A process for the preparation of a compound of formula (I) as defined in claim 1 which comprises:

(1) reacting a compound of the formula

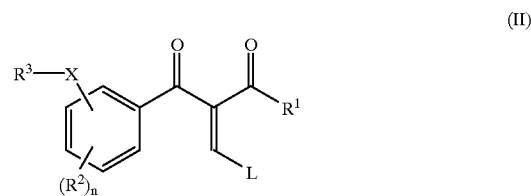

(II)

wherein L is a leaving group which is alkoxy or N,N-dialkylamino and wherein $R^1$, $R^2$, $R^3$ X and n are as defined in claim 1, provided that when X is $-NH-$, then $-XR^3$ is not in the ortho position of the phenyl ring, with hydroxylamine or a salt of hydroxylamine, to afford the corresponding compound of formula (I) wherein R is hydrogen, provided that when X is $-NH-$, then $-XR^3$ is not in the ortho position of the phenyl ring;

(2) reacting a salt of a compound of the formula

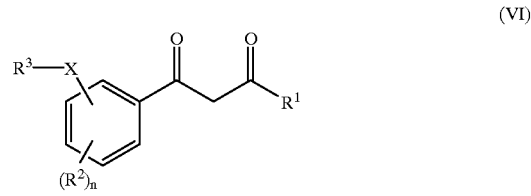

(VI)

wherein $R^1$, $R^2$, $R^3$, X and n are as defined in claim 1, provided that when X is $-NH-$, then $-XR^3$ is not in the ortho position of the phenyl ring, with a compound of the formula

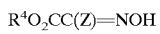

$R^4O_2CC(Z)=NOH$ wherein $R^4$ is as defined in claim 1 and Z is a halogen atom, to afford the corresponding compound of formula (I) wherein R is $-CO_2R^4$, provided that when X is $-NH-$, then $-XR^3$ is not in the ortho position of the phenyl ring; or (3) removing the protecting group under acidic or neutral reaction conditions from a compound of the formula

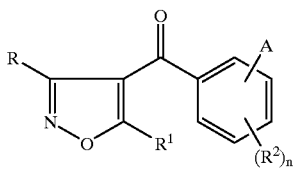

(VII)

wherein R, $R^1$, $R^2$ and n are as defined in claim 1, and A is in the ortho position of the phenyl ring and is $-NX^1R^3$ wherein $R^3$ is as defined in claim 1 and $X^1$ is a protecting group which is benzyl or t-butyloxycarbonyl, to afford the corresponding compound of formula (I) wherein X is $-NH-$ and $-XR^3$ is in the ortho position of the phenyl ring.

3. A compound according to claim 1 wherein:

R represents the hydrogen atom or a group $-CO_2R^4$;

$R^1$ represents:

a straight- or branched-chain alkyl group having up to six carbon atoms which is optionally substituted by one or more halogen atoms; or a cycloalkyl group having from three to six carbon atoms optionally substituted by one or more $R^5$ groups;

$R^2$ represents:

a straight- or branched-chain alkyl, alkenyl or alkynyl group having up to six carbon atoms optionally substituted by one or more halogen atoms;

a straight- or branched-chain alkyl group having up to six carbon atoms which is substituted by a group $-OR^5$;

a halogen atom;

phenyl optionally substituted by from one to three groups $R^{21}$ which are the same or different;

a group selected from $-COR^5$, nitro, cyano, $-CO_2R^5$, $-S(O)_pR^6$, $-O(CH_2)_mOR^5$, $-N(R^8)SO_2R^7$, $-CONR^9R^{10}$ and $-OR^{51}$;

$R^3$ represents $-S(O)_qR^7$;

X represents a group $-N(R^8)-$;

n represents zero or an integer from one to four; where n is greater than one the groups $R^2$ are the same or different;

$R^4$ represents a straight- or branched-chain alkyl group having up to six carbon atoms optionally substituted by one or more halogen atoms;

$R^5$ represents:

a straight- or branched-chain alkyl, alkenyl or alkynyl group having up to six carbon atoms optionally substituted by one or more halogen atoms; or a cycloalkyl group having from three to six carbon atoms;

$R^{51}$ represents:

a straight- or branched-chain alkyl, alkenyl or alkynyl group having up to six carbon atoms optionally substituted by one or more halogen atoms;

a cycloalkyl group having from three to six carbon atoms;

or phenyl optionally substituted by from one to five groups which are the same or different selected from a halogen atom, a straight- or branched-chain alkyl group having up to three carbon atoms optionally substituted by one or more halogen atoms; nitro, cyano, $-S(O)_pR^5$ and $-OR^5$;

$R^6$ represents:

a straight- or branched-chain alkyl, alkenyl or alkynyl group having up to six carbon atoms optionally substituted by one or more halogen atoms;

a cycloalkyl group having from three to six carbon atoms;

or phenyl optionally substituted by from one to five groups which are the same or different selected from a halogen atom, a straight- or branched-chain alkyl group having up to three carbon atoms optionally substituted by one or more halogen atoms; nitro, cyano, $-S(O)_pR^5$ and $-OR^5$;

$R^7$ represents:

a straight- or branched-chain alkyl alkenyl or alkynyl group having up to six carbon atoms optionally substituted by one or more halogen atoms;

a cycloalkyl group having from three to six carbon atoms;

phenyl optionally substituted by from one to five groups $R^{21}$ which are the same or different;

or $-NR^9R^{10}$;

$R^8$ represents:

the hydrogen atom; or a straight- or branched-chain alkyl, alkenyl or alkynyl group having up to six carbon atoms optionally substituted by one or more halogen atoms;

a cycloalkyl group having from three to six carbon atoms;

phenyl optionally substituted by from one to five groups which are the same or different selected from a halogen atom, a straight- or branched-chain alkyl group having up to three carbon atoms optionally substituted by one or more halogen atoms; nitro, cyano, $-S(O)_pR^5$ and $-OR^5$;

or a group $-OR^{11}$;

$R^9$ represents hydrogen or a straight- or branched-chain alkyl group having up to six carbon atoms optionally substituted by one or more halogen atoms;

$R^{11}$ represents a straight- or branched-chain alkyl group having up to six carbon atoms;

$R^{21}$ represents:

a halogen atom;

a straight- or branched-chain alkyl group having up to three carbon atoms optionally substituted by one or more halogen atoms; or a group selected from nitro, cyano, $-S(O)_pR^5$ and $-OR^5$;

m represents one, two or three;

p represents zero, one or two; and q represents two.

4. A compound according to claim 1 wherein:

R represents the hydrogen atom or a group $-CO_2R^4$;

$R^1$ represents:

a straight- or branched-chain alkyl group containing up to six carbon atoms which is optionally substituted by one or more halogen atoms; or a cycloalkyl group having from three to six carbon atoms optionally substituted by one or more $R^5$ groups or one or more halogen atoms;

$R^2$ represents:

a halogen atom;

a straight- or branched-chain alkyl group having up to six carbon atoms optionally substituted by one or more halogen atoms;

a straight- or branched-chain alkyl group having up to six carbon atoms which is substituted by one or more groups $-OR^5$;

a group selected from nitro, cyano, $-CO_2R^5$, $-S(O)_pR^6$, $-O(CH_2)_mOR^5$, $-COR^5$, $-NR^5R^6$, $-N(R^8)SO_qR^7$ and $-OR^{51}$;

$R^3$ represents —$S(O)_qR^7$;

X represents a group —$N(R^8)$—;

n represents zero or an integer from one to four; where n is greater than one the groups $R^2$ may be the same or different;

$R^4$ represents a straight- or branched-chain alkyl group having up to six carbon atoms which is optionally substituted by one or more halogen atoms;

$R^5$, $R^{51}$ and $R^6$, which may be the same or different, each represents:

the hydrogen atom;

a straight- or branched-chain alkyl group having up to six carbon atoms which is optionally substituted by one or more halogen atoms;

phenyl optionally substituted by from one to five groups $R^2$ which may be the same or different;

$R^7$ represents:

a straight- or branched-chain alkyl group having up to six carbon atoms which is optionally substituted by one or more halogen atoms;

phenyl optionally substituted by from one to five groups $R^{21}$ which may be the same or different; or a group —$NR^9R^{10}$;

$R^8$ represents:

the hydrogen atom;

a straight- or branched-chain alkyl, alkenyl or alkynyl group having up to ten carbon atoms which is optionally substituted by one or more halogen atoms; or phenyl optionally substituted from one to five groups which may be the same or different selected from nitro, halogen, $R^5$ and —$OR^5$;

$R^9$ and $R^{10}$, which may be the same or different, each represents:

the hydrogen atom;

a straight- or branched-chain alkyl group having up to six carbon atoms optionally substituted by one or more halogen atoms;

or phenyl optionally substituted by from one to five groups $R^2$ which may be the same or different;

$R^{21}$ represents:

a halogen atom;

a straight- or branched-chain alkyl group having up to three carbon atoms optionally substituted by one or more halogen atoms;

or a group selected from nitro, cyano, —$S(O)_pR^6$ and —$OR^5$;

p represents zero, 1 or 2;

q represents zero or 2; and m represents 1, 2 or 3.

5. A compound according to claim 1 wherein the 5- and 6-positions of the benzoyl ring are unsubstituted.

6. A compound according to claim 1 wherein the 2-position of the benzoyl ring is substituted.

7. A compound according to claim 1 wherein:

$R^1$ represents:

a straight- or branched-chain alkyl group having up to six carbon atoms which is optionally substituted by one or more halogen atoms; or a cycloalkyl group having from three to six carbon atoms optionally substituted by one or more methyl groups;

$R^2$ represents:

a halogen atom;

a straight- or branched-chain alkyl, alkenyl or alkynyl group having up to six carbon atoms optionally substituted by one or more halogen atoms;

a straight- or branched-chain alkyl group having up to six carbon atoms which is substituted by a group —$OR^5$;

phenyl optionally substituted by from one to three groups $R^{21}$ which are the same or different;

or a group selected from —$COR^5$, cyano, nitro, —$CO_2R^5$, —$S(O)_pR^6$, —$O(CH_2)_mOR^5$, —$N(R^8)SO_2R^7$ and —$OR^{51}$;

n represents zero or an integer from one to three; where n is greater than one the groups $R^2$ are the same or different;

$R^5$ represents:

a straight- or branched-chain alkyl group having up to six carbon atoms optionally substituted by one or more halogen atoms;

or a cycloalkyl group containing from three to six carbon atoms;

$R^{51}$ and $R^6$, which are the same or different, each represents:

a straight- or branched-chain alkyl or alkenyl group having up to six carbon atoms optionally substituted by one or more halogen atoms;

a straight- or branched-chain alkynyl group containing from three to six carbon atoms;

a cycloalkyl group containing three to six carbon atoms;

$R^7$ represents:

a straight- or branched-chain alkyl or alkenyl group having up to six carbon atoms optionally substituted by one or more halogen atoms;

a straight- or branched-chain alkynyl group containing from three to six carbon atoms;

a cycloalkyl group containing three to six carbon atoms; or phenyl optionally substituted by from one to three groups $R^{21}$ which may be the same or different;

$R^8$ represents:

the hydrogen atom; or a straight- or branched-chain alkyl or alkenyl group having up to six carbon atoms optionally substituted by one or more halogen atoms;

a straight- or branched-chain alkynyl group containing from three to six carbon atoms;

or a cycloalkyl group containing three to six carbon atoms;

$R^{21}$ represents:

a halogen atom;

a straight- or branched-chain alkyl group having up to three carbon atoms optionally substituted by one or more halogen atoms; or a group selected from nitro, cyano, —$S(O)_pR^5$ and —$OR^5$;

q represents two;

m represents two or three; and p represents zero, one or two.

8. A compound according to claim 1 wherein:

$R^1$ represents:

a straight- or branched-chain alkyl group having up to three carbon atoms; or a cycloallyl group having three or four carbon atoms optionally substituted by a methyl group;

$R^2$ represents:

a chlorine, bromine or fluorine atom; or a straight- or branched-chain alkyl, alkenyl or alkynyl group up to four carbon atoms optionally substituted by one or more halogen atoms;

a straight- or branched-chain alkyl group containing up to four carbon atoms which is substituted by a group —$OR^5$; or a group selected from —$COR^5$, —$CO_2R^5$, —$S(O)_pR^6$, —$O(CH_2)_mOR^5$, —$N(R^8)SO_2R^7$ and —$OR^{51}$;

$R^5$ and $R^6$, which are the same or different, each represents:

a straight- or branched-chain allyl group having up to four carbon atoms optionally substituted by one or more chlorine, bromine or fluorine atoms; or a cyclopropyl group;

$R^{51}$ and $R^7$, which may be the same or different, each represents:

a straight- or branched-chain alkyl or alkenyl group having up to four carbon atoms optionally substituted by one or more chlorine, bromine or fluorine atoms;

a straight- or branched-chain alkynyl group having three or four carbon atoms; or a cyclopropyl group;

$R^8$ represents:

the hydrogen atom;

a straight- or branched-chain alkyl or alkenyl group having up to four carbon atoms optionally substituted by one or more chlorine, bromine or fluorine atoms;

a straight- or branched-chain alkyl group having three or four carbon atoms; or a cyclopropyl group;

q represents two;

m represents two or three; and p represents zero, one or two.

9. A compound according to any one of claims 1 wherein:

$R^1$ represents methyl, ethyl, isopropyl, cyclopropyl or 1-methylcyclopropyl;

$R^2$ represents:

a bromine, chlorine or fluorine atom; or a straight- or branched-chain alkyl or alkenyl group having up to four carbon atoms optionally substituted by one or more chlorine, bromine or fluorine atoms;

a group selected from —$COR^5$, —$CO_2R^5$, —$SR^6$, —$O(CH_2)_mOR^5$, —$OR^{51}$ and —$N(R^8)SO_2R^7$; or a straight- or branched chain alkyl group having up to four carbon atoms which is substituted by —$OR^5$;

$R^5$ and $R^6$, which are the same or different, each represents a straight- or branched-chain alkyl group having up to three carbon atoms;

$R^{51}$ represents:

a straight- or branched-chain alkyl group having up to four carbon atoms optionally substituted by one or more chlorine, bromine or fluorine atoms;

a straight- or branched-chain alkenyl or alkynyl group having three or four carbon atoms; or a cyclopropyl group;

$R^7$ represents:

a straight- or branched-chain alkyl group having up to three carbon atoms optionally substituted by one or more chlorine, bromine, or fluorine atoms; or an allyl group optionally substituted by one or more chlorine, fluorine or bromine atoms;

$R^8$ represents:

the hydrogen atom;

a straight- or branched-chain alkyl group having up to three carbon atoms optionally substituted by one or more chlorine, bromine, or fluorine atoms; or an allyl group optionally substituted by one or more chlorine, fluorine or bromine atoms;

q represents two; and m represents two or three.

10. A compound according to claim 1 wherein

R represents hydrogen or —$CO_2Et$;

$R^1$ represents cyclopropyl;

$R^2$ represents a halogen atom or a group selected from nitro, trifluoromethyl, methyl, trifluoromethoxy, —$S(O)_pMe$ and —$N(R^8)SO_2R^7$;

$R^7$ represents a straight- or branched-chain alkyl group having up to three carbon atoms, phenyl or benzyl;

$R^8$ represents a straight- or branched-chain alkyl group having up to four carbon atoms, methoxy or phenyl;

p is zero, one or two;

n represents zero, one or two; and q represents two.

11. A compound according to claim 1 wherein a group —$XR^3$ is in the 2- or 4-position of the benzoyl ring.

12. A compound according to claim 1 wherein:

$R^1$ represents cyclopropyl;

$R^2$ represents a halogen atom;

$R^7$ represents methyl;

$R^8$ represents hydrogen or methyl; and n represents zero or one.

13. The compound according to claim 1 which is:

4-[2-chloro-4-(methylsulphonyl)aminobenzoyl]-5-cyclopropylisoxazole;

4-[4-chloro-2-(N-methyl-N-methylsulphonyl)aminobenzoyl]-5-cyclopropylisoxazole;

5-cyclopropyl-4-[2-(N-methyl-N-methylsulphonyl)aminobenzoyl]isoxazole;

4-[4-chloro-2-(N-ethyl-N-methylsulphonyl)aminobenzoyl]-5-cyclopropylisoxazole;

5-cyclopropyl-4-[2-(N-methyl-N-methylsulphonyl)amino-4-nitro-benzoyl]isoxazole;

5-cyclopropyl-4-[4-(N-methyl-N-methylsulphonyl)amino-2-nitro-benzoyl]isoxazole;

5-cyclopropyl-4-[4-methyl-2-(N-methyl-N-methylsulphonyl)amino-benzoyl]isoxazole;

4-[4-chloro-2-(N-n-propyl-N-methylsulphonyl)aminobenzoyl]-5-cyclopropylisoxazole;

5-cyclopropyl-4-[2-(N-ethyl-N-methylsulphonyl)amino-4-methylsulphonylbenzoyl]isoxazole;

5-cyclopropyl-4-[3,4-dichloro-2-(N-methyl-N-methylsulphonyl)-aminobenzoyl]isoxazole;

5-cyclopropyl-4-[2-(N-methyl-N-methylsulphonyl)amino-4-trifluoromethylbenzoyl]isoxazole;

5-cyclopropyl-4-[2-(N-phenyl-N-methylsulphonyl)aminobenzoyl]isoxazole;

4-[4-bromo-2-(N-methyl-N-methylsulphonyl)amino-benzoyl]-5-cyclopropylisoxazole;

5-cyclopropyl-4-[2-(N-methyl-N-methylsulphonyl)amino-4-methylsulphonylbenzoyl]isoxazole;

ethyl 5-cyclopropyl-4-[4-chloro-2-(N-methyl-N-methylsulphonylamino)benzoyl]isoxazole-3-carboxylate;

4-[4-chloro-2-(N-methyl-N-ethylsulphonylamino)benzoyl]-5-cyclopropyl-isoxazole;

5-cyclopropyl-4-[2,4-bis(N-methyl-N-methylsulphonyl)aminobenzoyl]isoxazole;

5-cyclopropyl-4-[2-(N-methyl-N-methylsulphonyl)amino-4-fluorobenzoyl]isoxazole;

4-[2-bromo-4-(N-methyl-N-methylsulphonyl)aminobenzoyl]-5-cyclopropylisoxazole;

4-[2-chloro-4-(N-methyl-N-methylsulphonyl)aminobenzoyl]-5-cyclopropylisoxazole;

4-[3-chloro-2-(N-methyl-N-methylsulphonyl)amino-4-trifluoromethoxybenzoyl]-5-cyclopropylisoxazole;

5-cyclopropyl-4-[2-(N-methyl-N-methylsulphonyl)amino-4-trifluoromethoxybenzoyl]isoxazole;

4-[5-chloro-2-(N-methyl-N-methylsulphonyl)aminobenzoyl]-5-cyclopropylisoxazole;

5-cyclopropyl-4-[2-fluoro-4-(N-methyl-N-methylsulphonyl)aminobenzoyl]isoxazole;

5-cyclopropyl-4-[3,4-difluoro-2-(N-methyl-N-methylsulphonyl)aminobenzoyl]isoxazole;

5-cyclopropyl-4-[4,5-difluoro-2-(N-methyl-N-methylsulphonyl)aminobenzoyl]isoxazole;

5-cyclopropyl-4-[4-iodo-2-(N-methyl-N-methylsulphonyl)aminobenzoyl]isoxazole;

4-[4-chloro-2-(N-isobutyl-N-methylsulphonyl)aminobenzoyl]-5-cyclopropylisoxazole;

4-[4-chloro-2-(N-methyl-N-n-propylsulphonyl)aminobenzoyl]-5-cyclopropylisoxazole;

4-[4-chloro-2-(N-methyl-N-phenylsulphonyl)aminobenzoyl]-5-cyclopropylisoxazole;

4-[4-chloro-2-(N-benzylsulphonyl-N-methyl)aminobenzoyl]-5-cyclopropylisoxazole;

4-[4-chloro-2-(N-methyl-N-isopropylsulphonyl)aminobenzoyl]-5-cyclopropylisoxazole;

4-[4-chloro-2-(N-methoxy-N-methylsulphonyl)aminobenzoyl]-5-cyclopropylisoxazole; or ethyl 5-cyclopropyl-4-[2-(N-methyl-N-methylsulphonyl)amino-4-trifluoromethylbenzoyl]isoxazole-3-carboxylate.

14. A herbicidal composition which comprises as active ingredient a herbicidally effective amount of a 4-benzoylisoxazole derivative of formula (I) as defined in claim 1 or an agriculturally acceptable salt thereof, in association with an agriculturally acceptable diluent or carrier and/or surface active agent.

15. A herbicidal composition according to claim 14 in the form of an aqueous suspension concentrate, a wettable powder, a water soluble or water dispersible powder, a liquid water soluble concentrate, a liquid emulsifiable suspension concentrate, a granule or an emulsifiable concentrate.

16. A method for controlling the growth of weeds at a locus which comprises applying to the locus a herbicidally effective amount of a 4-benzoylisoxazole derivative of formula (I) as defined in claim 1 or an agriculturally acceptable salt thereof.

17. A method according to claim 16 in which the locus is an area used, or to be used, for growing of crops and the compound is applied at an application rate from 0.01 kg to 4.0 kg per hectare.

18. A compound according to claim 3 wherein the 5- and 6-positions of the benzoyl ring are unsubstituted.

19. A compound according to claim 4 wherein the 5- and 6-positions of the benzoyl ring are unsubstituted.

20. A compound according to claim 3 wherein the 2-position of the benzoyl ring is substituted.

21. A compound according to claim 4 wherein the 2-position of the benzoyl ring is substituted.

22. A compound according to claim 5 wherein the 2-position of the benzoyl ring is substituted.

23. A compound according to claim 18 wherein the 2-position of the benzoyl ring is substituted.

24. A compound according to claim 19 wherein the 2-position of the benzoyl ring is substituted.

25. A compound according to claim 7 wherein the 5- and 6-positions of the benzoyl ring are unsubstituted.

26. A compound according to claim 7 wherein the 2-position of the benzoyl ring is substituted.

27. A compound according to claim 25 wherein the 2-position of the benzoyl ring is substituted.

28. A compound according to claim 8 wherein the 5- and 6-positions of the benzoyl ring are unsubstituted.

29. A compound according to claim 8 wherein the 2-position of the benzoyl ring is substituted.

30. A compound according to claim 28 wherein the 2-position of the benzoyl ring is substituted.

31. A compound according to claim 9 wherein the 5- and 6-positions of the benzoyl ring are unsubstituted.

32. A compound according to claim 9 wherein the 2-position of the benzoyl ring is substituted.

33. A compound according to claim 31 wherein the 2-position of the benzoyl ring is substituted.

34. A compound according to claim 3 wherein a group —$XR^3$ is in the 2- or 4-position of the benzoyl ring.

35. A compound according to claim 4 wherein a group —$XR^3$ is in the 2- or 4-position of the benzoyl ring.

36. A compound according to claim 5 wherein a group —$XR^3$ is in the 2- or 4-position of the benzoyl ring.

37. A compound according to claim 6 wherein a group —$XR^3$ is in the 2- or 4-position of the benzoyl ring.

38. A compound according to claim 9 wherein a group —$XR^3$ is in the 2- or 4-position of the benzoyl ring.

39. A compound according to claim 8 wherein a group —$XR^3$ is in the 2- or 4-position of the benzoyl ring.

40. A compound according to claim 9 wherein a group —$XR^3$ is in the 2- or 4-position of the benzoyl ring.

41. A compound according to claim 10 wherein a group —$XR^3$ is in the 2- or 4-position of the benzoyl ring.

42. A compound according to claim 12 wherein the 5- and 6-positions of the benzoyl ring are unsubstituted.

43. A compound according to claim 12 wherein the 2-position of the benzoyl ring is substituted.

44. A compound according to claim 12 wherein a group —$XR^3$ is in the 2- or 4-position of the benzoyl ring.

* * * * *